United States Patent
Kutyavin et al.

(10) Patent No.: US 11,840,728 B2
(45) Date of Patent: *Dec. 12, 2023

(54) INHIBITION OF NUCLEIC ACID POLYMERASES BY ENDONUCLEASE V-CLEAVABLE OLIGONUCLEOTIDE LIGANDS

(71) Applicant: Cepheid, Sunnyvale, CA (US)

(72) Inventors: Igor V. Kutyavin, Woodinville, WA (US); Sergey G. Lokhov, Bothell, WA (US)

(73) Assignee: Cepheid, Sunnyvale, CA (US)

( * ) Notice: Subject to any disclaimer, the term of this patent is extended or adjusted under 35 U.S.C. 154(b) by 123 days.

This patent is subject to a terminal disclaimer.

(21) Appl. No.: 17/508,379

(22) Filed: Oct. 22, 2021

(65) Prior Publication Data

US 2022/0119861 A1   Apr. 21, 2022

Related U.S. Application Data

(62) Division of application No. 16/914,158, filed on Jun. 26, 2020, now Pat. No. 11,155,859, which is a division of application No. 16/210,510, filed on Dec. 5, 2018, now Pat. No. 10,724,083.

(60) Provisional application No. 62/595,451, filed on Dec. 6, 2017.

(51) Int. Cl.
| | | |
|---|---|---|
| C07H 21/02 | (2006.01) | |
| C12Q 1/686 | (2018.01) | |
| C12N 15/115 | (2010.01) | |
| C12N 9/22 | (2006.01) | |
| C12N 9/12 | (2006.01) | |
| C12N 15/113 | (2010.01) | |

(52) U.S. Cl.
CPC ........... *C12Q 1/686* (2013.01); *C12N 9/1252* (2013.01); *C12N 9/22* (2013.01); *C12N 15/113* (2013.01); *C12N 15/115* (2013.01); *C12Y 301/21007* (2013.01); *C12N 2310/16* (2013.01); *C12N 2310/531* (2013.01); *C12Y 207/07007* (2013.01)

(58) Field of Classification Search
CPC .......................... C12N 15/113; C12N 2310/16
See application file for complete search history.

(56) References Cited

U.S. PATENT DOCUMENTS

| | | | |
|---|---|---|---|
| 3,721,725 A | 3/1973 | Briggs | |
| 4,683,195 A | 7/1987 | Mullis | |
| 4,683,202 A | 7/1987 | Mullis | |
| 5,270,184 A | 12/1993 | Walker | |
| 5,693,502 A | 12/1997 | Gold | |
| 5,801,155 A | 9/1998 | Kutyavin | |
| 5,824,517 A | 10/1998 | Cleuziat | |
| 5,854,033 A | 12/1998 | Lizardi | |
| 6,063,603 A | 5/2000 | Davey | |
| 6,127,121 A | 10/2000 | Meyer, Jr. | |
| 6,214,587 B1 | 4/2001 | Dattagupta | |
| 6,251,639 B1 | 6/2001 | Kurn | |
| 6,410,278 B1 | 6/2002 | Notomi | |
| 7,794,945 B2 | 9/2010 | Hedgpeth | |
| 8,143,006 B2 | 3/2012 | Kutyavin | |
| 8,349,556 B2 | 1/2013 | Kutyavin | |

FOREIGN PATENT DOCUMENTS

EP   3083961 B1   7/2018

OTHER PUBLICATIONS

Jayasena, S.D., "Aptamers: An Emerging Class of Molecules That Rival Antibodies in Diagnostics," Clinical Chemistry 45(9):1628-1650, Sep. 1999.
Martin, F.H., et al., "Base Pairing Involving Deoxyinosine: Implications for Probe Design," Nucleic Acids Research 13(24):8927-8938, Dec. 20, 1985.
Skerra, A., "Phosphorothioate Primers Improve the Amplification of DNA Sequences by DNA Polymerases With Proofreading Activity," Nucleic Acids Research 20(14):3551-3554, Jul. 25, 1992.
Yakimovich, O.Y., "Influence of DNA Aptamer Structure on the Specificity of Binding to Taq DNA Polymerase," Biochemistry (Moscow) 68(2):228-235, Feb. 2003.
Yao, M., and Y.W. Kow, "Further Characterization of *Escherichia coli* Endonuclease V. Mechanism of Recognition for Deoxyinosine, Deoxyuridine, and Base Mismatches in DNA" The Journal of Biological Chemistry 272(49):30774-30779, Dec. 5, 1997.
Yoshizawa, S., "Nuclease Resistance of an Extraordinarily Thermostable Mini-Hairpin DNA Fragment, d(GCGAAGC) and its Application to In Vitro Protein Synthesis," Nucleic Acids Research 22(12):2217 2221, Jun. 25, 1994.

*Primary Examiner* — Amy H Bowman
(74) *Attorney, Agent, or Firm* — Barry L. Davison; Davis Wright Tremaine LLP

(57) ABSTRACT

Provided are methods and compositions for activating oligonucleotide aptamer-deactivated DNA polymerases, comprising cleaving the aptamer by endonuclease V enzymatic activity to reduce or eliminate binding of the oligonucleotide aptamer to the DNA polymerase, thereby activating DNA synthesis activity of the DNA polymerase in a reaction mixture. Mixtures for use in methods of the invention are also provided. In some aspects, the oligonucleotide aptamer comprises one or more deoxyinosine nucleotides providing for aptamer-specific recognition and cleavage of the aptamer by the endonuclease V enzymatic activity. Exemplary oligonucleotide aptamers, mixtures and methods employing endonuclease V enzymatic activity are provided. The methods can be practiced using kits comprising a DNA polymerase-binding oligonucleotide aptamer and at least one endonuclease V enzymatic activity having oligonucleotide aptamer-specific recognition to provide for specific cleavage of the aptamer by the endonuclease V enzymatic activity.

9 Claims, 9 Drawing Sheets

Specification includes a Sequence Listing.

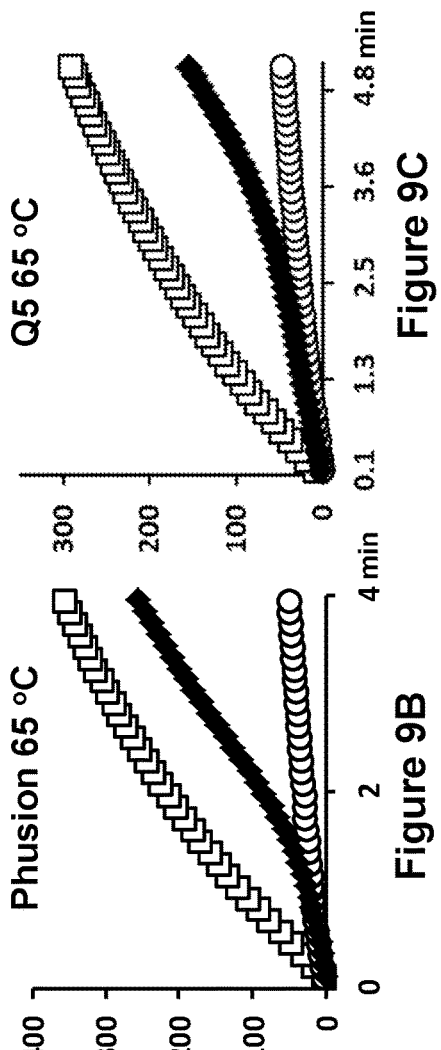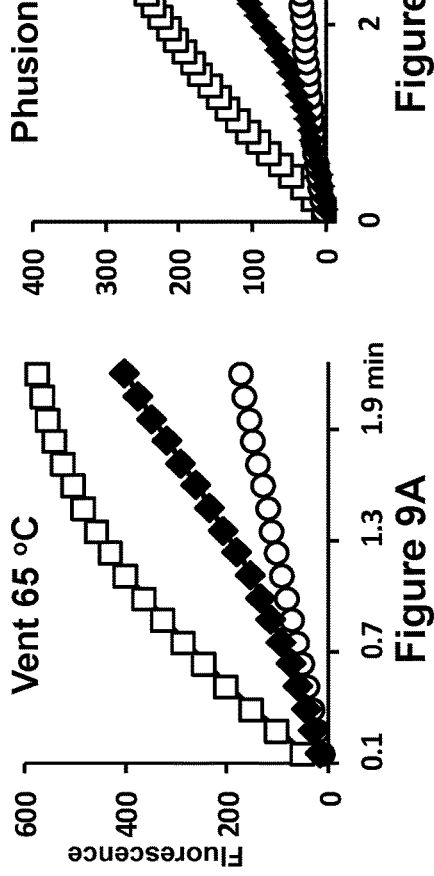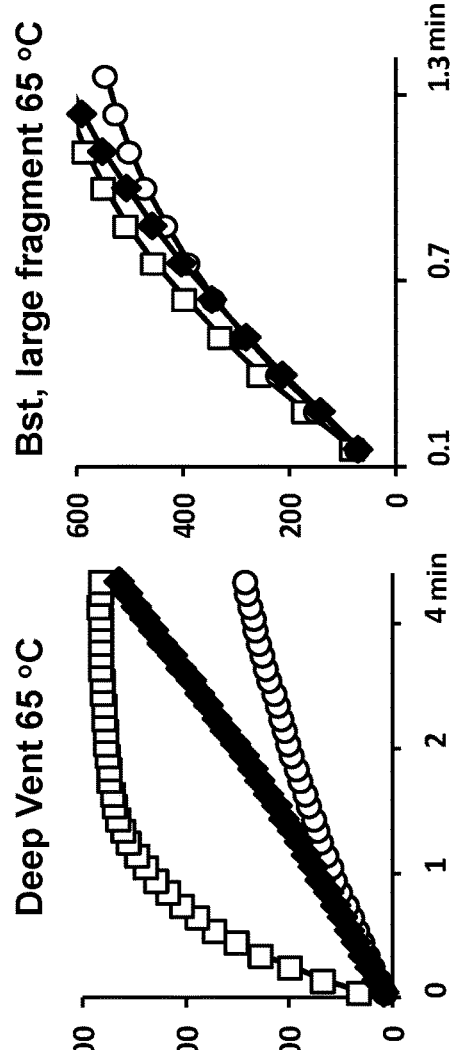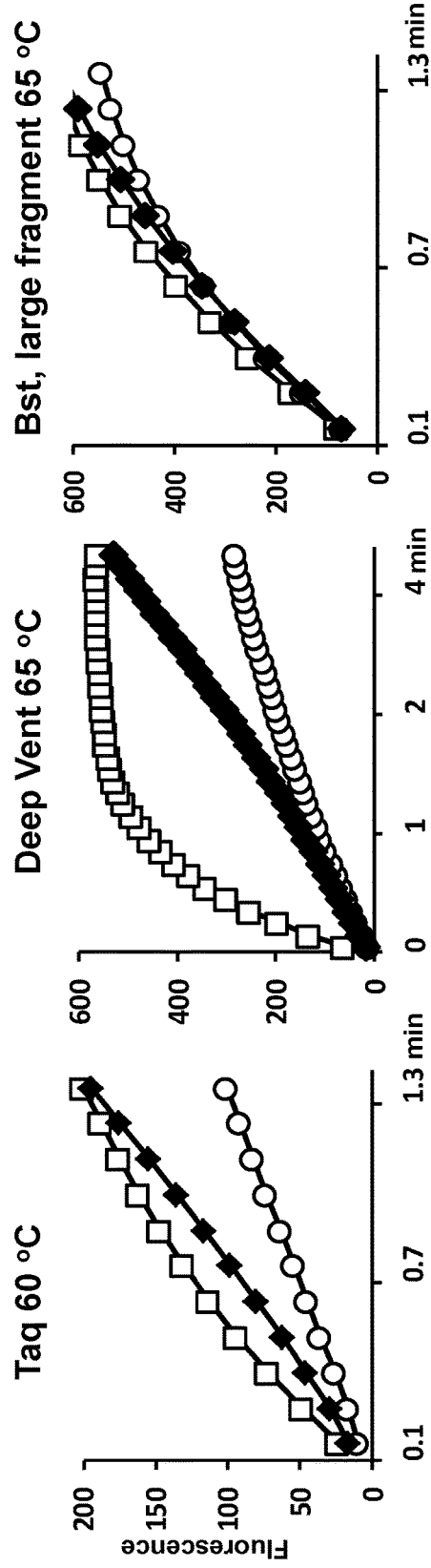

INHIBITION OF NUCLEIC ACID POLYMERASES BY ENDONUCLEASE V-CLEAVABLE OLIGONUCLEOTIDE LIGANDS

CROSS-REFERENCE TO RELATED APPLICATION

This application is a divisional of U.S. patent application Ser. No. 16/914,158, filed Jun. 26, 2020, issued as U.S. Pat. No. 11,155,859, which is a divisional of U.S. patent application Ser. No. 16/210,510, filed Dec. 5, 2018, issued as U.S. Pat. No. 10,724,083, which claims the benefit of U.S. Provisional Patent Application No. 62/595,451, filed Dec. 6, 2017, the disclosures of which are herein incorporated by reference in their entirety.

INCORPORATION OF SEQUENCE LISTING

The contents of the text file named "0102384-001US1 Sequence Listing.txt," which was created on Dec. 5, 2017, and is 11 KB in size, are hereby incorporated by reference in their entirety.

BACKGROUND

Aspects of the present invention relate generally to improved methods of blocking DNA polymerase activity with oligonucleotide aptamers at low reaction temperatures, and restoring the enzyme activity upon raising the reaction temperature (e.g., hot-start methods).

DNA polymerases are enzymes used for synthesis of DNA strands by primer extension, wherein the polymerase-catalyzed DNA synthesis may be initiated by oligonucleotide primers hybridized to a complementary template DNA. Initiating DNA synthesis from this template-hybridized primer, DNA polymerases create complementary DNA strands in the presence of corresponding nucleotide 5'-triphosphates. Sequence specificity of nucleotide polymerization, when the oligonucleotide primers bind exclusively to the desired sites and nowhere else, is an important requirement in many applications wherein DNA synthesis is used. However, the efficiency and fidelity of DNA synthesis can be reduced when primers hybridize to non-complementary DNAs, leading to synthesis of incorrect DNA sequences.

Many so-called 'Hot Start' methods have been developed to avoid incorrect primer extension products (e.g., see Paul, N., et al. (2010), for review). One of the most common techniques is based on use of oligonucleotide aptamers (Jayasena, S. D., 1999). Aptamers offer a number of advantages over other reported methods. Using a method of molecular evolution (SELEX), they can be quickly engineered in a test tube and then readily and inexpensively manufactured by chemical synthesis. Ideally, an aptamer should: (i) completely block DNA polymerase at low temperatures, and (ii) provide no blockage effect at the desired elevated reaction temperature. Unfortunately, this is very difficult, if not impossible to achieve, and the aptamer structure usually represents a compromise between these two key requirements. New methods, therefore, are needed to improve control of aptamer activity in reaction mixtures containing DNA polymerases.

Particular aspects provide methods of activating an aptamer-inactivated DNA polymerase, comprising: providing a reaction mixture suitable for DNA synthesis, the reaction mixture comprising (i) a DNA polymerase, (ii) an endonuclease V-cleavable oligonucleotide aptamer that binds to the DNA polymerase, wherein the oligonucleotide aptamer is present in an amount effective to inhibit DNA synthesis activity of the DNA polymerase in the reaction mixture, and (iii) an endonuclease V enzymatic activity; and cleaving the aptamer by the endonuclease V enzymatic activity to reduce or eliminate binding of the oligonucleotide aptamer to the DNA polymerase, thereby activating the DNA synthesis activity of the DNA polymerase, to increase DNA synthesis in the reaction mixture. In the methods, cleaving may be facilitated using a reaction temperature that facilitates both DNA polymerase activity and the endonuclease V enzymatic activity. In the methods, cleaving may be facilitated by increasing the temperature of the reaction mixture from a first temperature to a second temperature that more strongly facilitates the endonuclease V enzymatic activity. In the methods, providing a reaction mixture suitable for DNA synthesis may comprise dissolving a dried form of at least one of said (i) DNA polymerase, (ii) endonuclease V-cleavable oligonucleotide aptamer, and (iii) endonuclease V enzymatic activity into an aqueous solution. DNA synthesis in the methods may result in DNA amplification in the reaction mixture (e.g., wherein the DNA amplification comprises PCR) DNA synthesis in the methods may comprise an isothermal amplification reaction. The methods may comprise detecting the presence of a target DNA and/or measuring an amount of a target DNA in the reaction mixture. In the methods, the oligonucleotide aptamer may comprise one or more deoxyinosine nucleotides. In the methods, the oligonucleotide aptamer may have a stem-loop structure, wherein one or more deoxyinosine nucleotides may be incorporated into the stem segment of the stem-loop structure, and/or wherein one or more deoxyinosine nucleotides may be incorporated into the loop segment of the stem-loop structure. In the methods, the loop of the stem-loop structure, may, for example, comprise a nucleotide sequence selected from the group consisting of 5'-TTCITAGCGTTT-3' (SEQ ID NO:22), 5'-TTCTI-AGCGTTT-3' (SEQ ID NO:23), 5'-TTCTTAICGTTT-3' (SEQ ID NO:24), 5'-TTCIIAGCGTTT-3' (SEQ ID NO:25), 5'-TTCITAICGTTT-3' (SEQ ID NO:26), 5'-TTCTIA-ICGTTT-3' (SEQ ID NO:27), and 5'-TTCIITAICGTTT-3' (SEQ ID NO:28). In the methods, the loop of the stem-loop structure may, for example, comprise one of the nucleotide sequences 5'-TTCITAGCGTTT-3' (SEQ ID NO:22), 5'-TTCTIAGCGTTT-3' (SEQ ID NO:23) or 5'-TTCTTA-ICGTTT-3' (SEQ ID NO:24). In the methods, the endonuclease V enzymatic activity may comprise, for example, *Thermotoga maritima* endonuclease V enzymatic activity.

Additional aspects provide kits for activating an aptamer-inactivated DNA polymerase, comprising: an endonuclease V enzymatic activity; and a DNA polymerase-binding oligonucleotide aptamer cleavable by an endonuclease V enzymatic activity. In the kits, the oligonucleotide aptamer may comprise one or more deoxyinosine nucleotides. In the kits, the oligonucleotide aptamer may comprise a stem-loop structure. In the kits, one or more deoxyinosine nucleotides may be located in the stem segment of the stem-loop structure, and/or one or more deoxyinosine nucleotides may be located in the loop segment of the stem-loop structure. In the kits, the loop of the stem-loop structure, may, for example, comprise a nucleotide sequence selected from the group consisting of 5'-TTCITAGCGTTT-3' (SEQ ID NO:22), 5'-TTCTIAGCGTTT-3' (SEQ ID NO:23), 5'-TTCTTAICGTTT-3' (SEQ ID NO:24), 5'-TTCI-IAGCGTTT-3' (SEQ ID NO:25), 5'-TTCITAICGTTT-3' (SEQ ID NO:26), 5'-TTCTIAICGTTT-3' (SEQ ID NO:27), and 5'-TTCIITAICGTTT-3' (SEQ ID NO:28). In the kits, the loop of the stem-loop structure may, for example, comprise one of the nucleotide sequences 5'-TTCITAGCGTTT-3' (SEQ ID NO:22), 5'-TTCTIAGCGTTT-3' (SEQ ID NO:23) or 5'-TTCTTAICGTTT-3' (SEQ ID NO:24). In the kits, the endonuclease V enzymatic activity may comprise, for example, *Thermotoga maritima* endonuclease V enzymatic activity.

Further aspects provide reaction mixtures for use in a method of DNA synthesis, which reaction mixture comprises: a DNA polymerase; an endonuclease V-cleavable oligonucleotide aptamer that binds reversibly to the DNA polymerase, wherein the oligonucleotide aptamer is present in an amount effective to inhibit DNA synthesis activity of the DNA polymerase in the reaction mixture; and an endonuclease V enzymatic activity capable of cleaving (or effective to cleave) the oligonucleotide aptamer to reduce or eliminate binding of the oligonucleotide aptamer to the DNA polymerase, thereby activating the DNA synthesis activity of the DNA polymerase. In the reaction mixtures, the DNA polymerase activity and/or the endonuclease V enzymatic activity may be temperature-dependent. In the reaction mixtures, the endonuclease V enzymatic activity may increase when the reaction mixture is heated from a first temperature value to a second temperature value that promotes the endonuclease V enzymatic activity. In the reaction mixtures, the DNA polymerase, oligonucleotide aptamer, and endonuclease V enzymatic activity may be in a dried state. In the reaction mixtures, the oligonucleotide aptamer may comprise one or more deoxyinosine nucleotides. In the reaction mixtures, the oligonucleotide aptamer may comprise a stem-loop structure. In the reaction mixtures, one or more deoxyinosine nucleotides may be located in the stem segment of the stem-loop structure, and/or one or more deoxyinosine nucleotides may be located in the loop segment of the stem-loop structure. In the reaction mixtures, the loop of the stem-loop structure, may, for example, comprise a nucleotide sequence selected from the group consisting of 5'-TTCITAGCGTTT-3' (SEQ ID NO:22), 5'-TTCTIAGCGTTT-3' (SEQ ID NO:23), 5'-TTCTTAICGTTT-3' (SEQ ID NO:24), 5'-TTCIIAGCGTTT-3' (SEQ ID NO:25), 5'-TTCITAICGTTT-3' (SEQ ID NO:26), 5'-TTCTIAICGTTT-3' (SEQ ID NO:27), and 5'-TTCIITAICGTTT-3' (SEQ ID NO:28). In the reaction mixtures, the loop of the stem-loop structure may, for example, comprise one of the nucleotide sequences 5'-TTCITAGCGTTT-3' (SEQ ID NO:22), 5'-TTCTIAGCGTTT-3' (SEQ ID NO:23) or 5'-TTCTTAICGTTT-3' (SEQ ID NO:24). In the reaction mixtures, the endonuclease V enzymatic activity may comprise, for example, *Thermotoga maritima* endonuclease V enzymatic activity. The reaction mixtures may further comprise one or more of dATP, dCTP, dGTP, and/or dTTP, and/or $Mg^{2+}$ ion.

Yet further aspects provide oligonucleotide aptamers, comprising a nucleic acid sequence that forms a hairpin structure, having a stem and a loop portion, that binds to a DNA polymerase, wherein the stem and/or the loop portion comprises one or more deoxyinosine nucleotides, and wherein the loop portion comprises a nucleotide sequence 5'-TTCTTAGCGTTT-3' (SEQ ID NO:21) that may be substituted with deoxyinosine at one or more of positions 4, 5, and 7. In the oligonucleotide aptamers, the loop portion may comprise the nucleotide sequence 5'-TTCTTAGCGTTT-3' (SEQ ID NO:21). In the oligonucleotide aptamers, one or more deoxyinosine nucleotides may be located in the stem segment of the stem-loop structure, and/or one or more deoxyinosine nucleotides may be located in the loop segment of the stem-loop structure. In the oligonucleotide aptamers, the loop of the stem-loop structure, may, for example, comprise a nucleotide sequence selected from the group consisting of 5'-TTCITAGCGTTT-3' (SEQ ID NO:22), 5'-TTCTIAGCGTTT-3' (SEQ ID NO:23), 5'-TTCTTAICGTTT-3' (SEQ ID NO:24), 5'-TTCI-IAGCGTTT-3' (SEQ ID NO:25), 5'-TTCITAICGTTT-3' (SEQ ID NO:26), 5'-TTCTIAICGTTT-3' (SEQ ID NO:27), and 5'-TTCIITAICGTTT-3' (SEQ ID NO:28). In the oligonucleotide aptamers, the loop of the stem-loop structure may, for example, comprise one of the nucleotide sequences 5'-TTCITAGCGTTT-3' (SEQ ID NO:22), 5'-TTCTI-AGCGTTT-3' (SEQ ID NO:23) or 5'-TTCTTAICGTTT-3' (SEQ ID NO:24). In the oligonucleotide aptamers, the one or more deoxyinosine nucleotides may render the oligonucleotide aptamer cleavable by an endonuclease V enzymatic activity (e.g., wherein the endonuclease V enzymatic activity may comprise *Thermotoga maritima* endonuclease V enzymatic activity).

Still further aspects provide compositions comprising a DNA polymerase complexed with an oligonucleotide aptamer as disclosed herein.

BRIEF DESCRIPTION OF THE DRAWINGS

FIGS. 9A through 9F show, according to particular exemplary aspects, endonuclease V-induced activation of Taq (FIG. 9D), Phusion® (FIG. 9B), Q5® (FIG. 9C), Vent® (FIG. 9A), Deep Vent® (FIG. 9E) and Bst large fragment (FIG. 9F) DNA polymerases that were initially deactivated (i.e., "inhibited" or "blocked") by the presence of aptamer SEQ ID NO:6 (♦ curves). FIGS. 9A through 9F also show the change of fluorescence with time in the absence of endonuclease V for the aptamer-blocked (○) and unblocked (□) DNA polymerase. The DNA polymerase activity was monitored by extension of the self-priming hairpin-like fluorescent probe SEQ ID NO:29 (see FIG. 8), which was present in the reaction mixture with all four dNTPs in a magnesium-containing buffer. In all cases experiments were performed at 60 or 65° C., as indicated in each figure. The structure of aptamer SEQ ID NO:6 is shown in FIG. 2, and details of the experimental setup, results analysis and conclusions are provided below in "Example 3."

DETAILED DESCRIPTION

Figure 1:
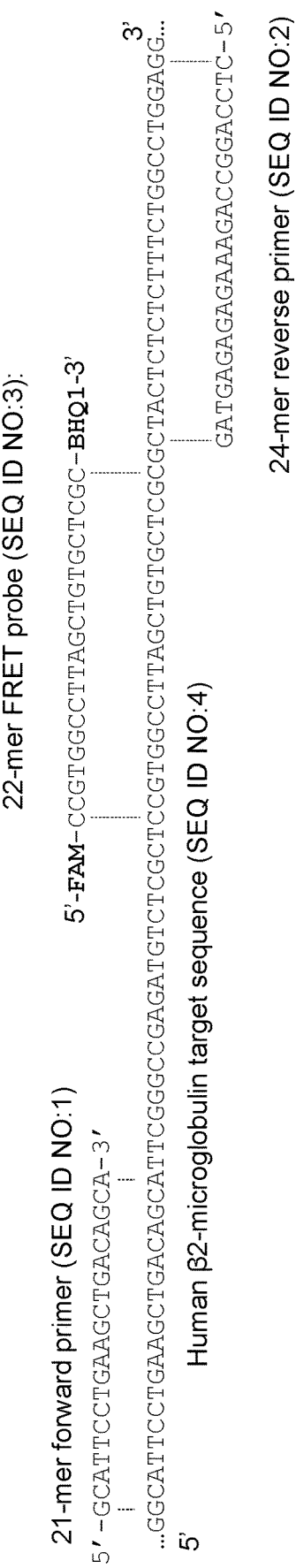
FIG. 1 shows, according to particular exemplary aspects, a portion of a human β2-microglobulin gene sequence (SEQ ID NO:4), forward and reverse primers (SEQ ID NOS:1-2, respectively) and a 22-mer fluorescent probe (SEQ ID NO:3), which were used in exemplary 5'-nuclease PCR assays of the present invention from which exemplary results are shown in FIGS. 3, 5, and 7. The primers and probe are shown aligned with an amplified β2-microglobulin fragment sequence in 5'→3' orientation as indicated.

Definitions:

Terms and symbols of biochemistry, nucleic acid chemistry, molecular biology and molecular genetics used herein follow those of standard treatises and texts in the field (e.g., Sambrook, J., et al., 1989; Kornberg, A. and Baker, T., 1992; Gait, M. J., ed., 1984; Lehninger, A. L., 1975; Eckstein, F., ed., 1991, and the like). To facilitate understanding of particular exemplary aspects of the invention, a number of terms are discussed below.

In particular aspects, "aptamer" or "oligonucleotide aptamer" refers herein to an oligonucleotide that is capable of binding to a DNA polymerase and blocking its DNA synthesis enzymatic activity. The aptamers can be linear molecules and/or capable to form secondary structures such as hairpin or stem-loop structures, etc. Examples of aptamers and methods of selection (design) can be found, for instance, in Yakimovich, O. Yu., et al., (2003); Jayasena, S. D. (1999); U.S. Pat. No. 5,693,502 to Gold, L. and Jayasena, S. D., which are incorporated here by reference. The phrase "aptamer, that binds to the DNA polymerase, in an amount sufficient to inhibit DNA synthesis activity of the DNA polymerase," as used herein, means that the DNA synthesis activity of the DNA polymerase is at least partially inhibited (e.g., inhibited to a level in the range of from about 1% to about 99.99%). Any level of aptamer inhibition of the DNA synthesis activity of the DNA polymerase can provide an advantage for DNA synthesis, and thus according to particular preferred hot start aspects of the present invention, the DNA synthesis activity of the DNA polymerase is substantially inhibited (e.g., inhibited to a level in the range of about 80% to 99.99%, or to any subrange or level therein), or completely (100%) inhibited, providing an advantage over other 'hot start' technologies (e.g., Paul, N., et al., 2010). Likewise, in the disclosed methods, "cleaving the aptamer by the Endonuclease V enzymatic activity to reduce or eliminate the binding of the oligonucleotide aptamer to the DNA polymerase and activate the DNA synthesis activity of the DNA polymerase" is preferably complete (100%) or substantially complete (e.g., inhibited to a level in the range of about 80% to 99.99%, or to any subrange or level therein), but can be partial (e.g., inhibited to a level in the range of from about 1% to about 99.99%), as exemplified herein (e.g., FIGS. 3, 5, 7, and 9).

An oligonucleotide aptamer may comprise ribo- or 2'-deoxyribonucleotides or a combination thereof. Oligonucleotide aptamers may be modified. Regarding the aptamers herein, the terms "modified" and "modification" are used in two different aspects, wherein the aptamers can be (i) modified synthetically, e.g. during the oligonucleotide synthesis, and (ii) enzymatically-modified in the context of or during DNA synthesis reactions. Synthetically, the aptamers may incorporate any kind and/or number of structural modifications across the length of the aptamer (e.g., in the middle or at the ends of the oligonucleotide chain). The term "structural modifications" refers to any chemical substances such as atoms, moieties, residues, polymers, linkers or nucleotide analogs, etc., which are usually of a synthetic nature and which are not commonly present in naturally-occurring nucleic acids. As used herein, the term "structural modifications" also include nucleoside or nucleotide analogs which are rarely present in naturally-occurring nucleic acids including but not limited to inosine, 5-bromouracil, 5-methylcytosine, 5-iodouracil, 2-aminoadenosine, 6-methyladenosine, pseudouridine, deoxyuridine, and the like. In particular embodiments, the aptamers incorporate one or more deoxyinosine (deoxyriboinosine) nucleotides that enable an endonuclease V enzyme to recognize the oligonucleotide aptamer as a substrate and modify its structure by cleavage. Nucleotides in the aptamers may be modified at the phosphates, sugar moieties or nucleotide bases. The structural modifications can be "duplex-stabilizing modifications."

"Duplex-stabilizing modifications" refer to structural modifications, the presence of which in double-stranded nucleic acids provides a duplex-stabilizing effect when compared in thermal stability, usually measured as "Tm," with respective nucleic acid complexes that have no such structural modification and, e.g., comprise natural nucleotides. Duplex-stabilizing modifications are structural modifications that are most commonly applied in synthesis of probes and primers, as represented by modified nucleotides and 'tails' like intercalators and minor groove binders as, for example, disclosed in U.S. Pat. No. 8,349,556 to Kutyavin, I. V.; U.S. Pat. No. 7,794,945 to Hedgpeth, J. et al.; U.S. Pat. No. 6,127,121 to Meyer, Jr., R. B., et al.; U.S. Pat. No. 5,801,155 to Kutyavin, I. V., et al., and the references cited in. Duplex-stabilizing modifications can be used to prepare aptamers of the invention, for example, to improve thermal stability of stem (duplex) structures of hairpin-like aptamers. In preferred methods of the invention, the oligonucleotide aptamers are modified in (e.g., during) DNA synthesis reactions using enzymatic activity of one or more aptamer-modifying enzyme(s). In this aspect, the terms "modify," "modification," and "structural modifications" mean changes in the initial chemical structure of the aptamers. The change is triggered by Endonuclease V enzymes, resulting in a cleavage of one or more phosphodiester bonds. In the methods of the invention, these Endonuclease V-triggered structural modifications reduce or eliminate the ability of the oligonucleotide aptamer to bind to the DNA polymerase and block or reduce its activity in the reaction. In certain aspects, oligonucleotide aptamers comprise one or more deoxyinosine nucleotides, and aptamer modification results from aptamer cleavage (phosphodiester bond cleavage) by endonuclease V, at the second phosphodiester bond in the DNA strand on the 3' side of a deoxyinosine nucleotide.

In particular aspects, the term "secondary structure" refers to an intramolecular complex formation of one sequence in a poly- or oligonucleotide with another sequence in the same polymer due to complete or partial complementarity between these two sequences formed based on the principal rules of Watson-Crick base pairing. The terms "hairpin" structure and "stem-loop" structure as referred to herein describe elements of secondary structure, and both terms refer to a double-helical region (stem) formed by base pairing between complementary sequences within a single strand RNA or DNA.

As used herein, the term "nuclease" refers to an enzyme that expresses a phosphomonoesterase or phosphodiesterase activity and is capable of cleaving a phosphoester bond in compounds such as R'—O—P(O)(OH)$_2$ and R'—O—P(O)(OH)—O—R," resulting in products R'—OH+P(O)(OH)$_3$ and R'—OH+P(O)(OH)$_2$—O—R" (or R"—OH+P(O)(OH)$_2$—O—R'), respectively, and wherein R' and R" may be moieties of any structure which are not necessarily of a nucleotide nature. The term "nucleases" incorporates both "exo" and "endo" nucleases. In certain aspects, endonuclease V is used to cleave phosphodiester bonds of oligonucleotide aptamers comprising one or more deoxyinosine nucleotides.

The term "aptamer-modifying enzymatic activity" refers to an aptamer-modifying enzyme or mixture of aptamer-modifying enzymes which recognize an aptamer of the invention as a substrate and modifies its structure so that the inhibitory activity of the aptamer is substantially disabled. In particular aspects, this recognition is directed by presence of one or more deoxyinosine nucleotides within the aptamer structure. These aptamer structural modifications caused by endonuclease V enzymatic activity reduce the ability of the oligonucleotide aptamer to bind to the DNA polymerase and to block or reduce the polymerase activity in the reaction mixture.

As used herein, the term "deoxyinosine" refers to deoxyinosine and structural modifications of deoxyinosine, including but not limited to 7-deaza-deoxyinosine, 8-aza-7-deaza-deoxyinosine and other structural modifications of deoxyinosine, and including various ribonucleotide derivatives thereof, which can be recognized and cleaved by an endonuclease V enzymatic activity.

As used herein, the term "deoxyuridine" refers to deoxyuridine and structural modifications of deoxyuridine, including various ribonucleotide derivatives thereof, that can be recognized and cleaved by an endonuclease V enzymatic activity.

As used herein, the term "endonuclease V" refers to repair enzymes that recognize deoxyinosine in DNA, and hydrolyze the second phosphodiester bond in the DNA strand on the 3' side of a deoxyinosine nucleotide (see, e.g., U.S. Pat. No. 8,143,006 to Kutyavin, I. V.).

The term "DNA polymerase" refers to an enzyme that catalyzes synthesis of deoxyribo nucleic acids (DNAs), most commonly double-stranded DNAs, using single-stranded DNAs as "templates." The DNA synthesis is usually initiated by an oligonucleotide primer that is hybridized to a complementary template strand. Starting from this template-hybridized primer, DNA polymerase creates a Watson-Crick complementary strand in the presence of 2'-deoxyribonucleotide 5'-triphosphates (dNTPs). The term "DNA polymerase," as used herein, also incorporates "reverse transcriptases," enzymes which can perform DNA synthesis using single-stranded ribonucleic acids (RNAs) as template strands.

"Polynucleotide" and "oligonucleotide" are used herein interchangeably and in each case means a linear polymer of nucleotide monomers. Polynucleotides typically range in size from a few monomeric units, e.g., 5-60, when they are usually referred to as "oligonucleotides," to several thousand monomeric units. The exact size will depend on many factors, which in turn depends on the ultimate function or use of the oligonucleotide. The oligonucleotides may be generated in any manner, including chemical synthesis, DNA replication, reverse transcription, or a combination thereof. Unless otherwise specified, whenever a polynucleotide or oligonucleotide is represented by a sequence of letters, for example, "TTCTTAGCGTTT (SEQ ID NO:21)," it is understood herein, unless otherwise specified in the text, that the nucleotides are in 5'→3' order from left to right and that "A" denotes deoxyadenosine, "C" denotes deoxycytidine, "G" denotes deoxyguanosine, and "T" denotes deoxythymidine. Usually DNA polynucleotides comprise these four deoxyribonucleosides linked by phosphodiester linkage whereas RNA comprises uridine ("U") in place of "T" for the ribose counterparts.

The terms "oligonucleotide primer" and/or "primer" refer to a single-stranded DNA or RNA molecule that hybridizes to a complementary target nucleic acid and serves to prime enzymatic synthesis of a second nucleic acid strand in the presence of a DNA polymerase. In this case, the target nucleic acid "serves as a template" for the oligonucleotide primer.

In particular aspects, the terms "complementary" or "complementarity" are used herein in reference to the polynucleotide base-pairing rules. Double-stranded DNA, for example, consists of base pairs wherein, for example, G complexes or pairs with C via formation of a three hydrogen bond complex, and A complexes or pairs with T via formation of a two hydrogen bond complex, such that G is regarded as being complementary to C and A is regarded as being complementary to T. In this sense, for example, an oligonucleotide 5'-GATTTC-3' is complementary to the sequence 3'-CTAAAG-5' via intrastrand G:C and A:T hydrogen bonding interactions. Complementarity may be "partial" or "complete." In partial complementarity, only some of the nucleic acids bases are matched according to the base pairing rules. "Complementarity" may also be used in reference to individual nucleotides and oligonucleotide sequences within the context of polynucleotides (e.g., interstrand complementarity). The terms "complementary" and "complementarity" refer to the most common type of complementarity in nucleic acids, namely, Watson-Crick base pairing as described above, although the oligonucleotides may alternately participate in other types of "non-canonical" pairings like Hoogsteen, wobble and G-T mismatch pairing.

The term "natural nucleosides" refers to the four standard 2'-deoxyribonucleosides (usually named herein as "deoxynucleosides" or "deoxyribonucleosides") that are found in DNAs isolated from natural sources. Natural nucleosides are deoxyadenosine, deoxycytidine, deoxyguanosine, and deoxythymidine. The term also encompasses their ribose counterparts, with uridine (U) in place of thymidine. The same name variations are applied herein to "natural nucleotides."

As used herein, the terms "unnatural nucleosides" or "modified nucleosides" refer to nucleoside analogs that are different in their structure from those natural nucleosides for DNA and RNA polymers. Some naturally occurring nucleic acids contain nucleosides that are structurally different from the natural nucleosides defined above, for example, DNAs of eukaryotes may incorporate 5-methyl-cytosine, and tRNAs contain many nucleoside analogs. However, as used herein, the terms "unnatural nucleosides" or "modified nucleosides" encompasses these nucleoside modifications even though they can be found in natural sources.

The term "reaction mixture" generally means herein a solution containing all necessary reactants for performing DNA synthesis such as a DNA polymerase, oligonucleotide primer(s), template polynucleotide, deoxyribonucleoside 5'-triphosphates, reaction cofactors (e.g., magnesium or manganese ions), etc. The reaction mixture can incorporate other reaction components that help to improve DNA synthesis (e.g., buffering and salt components, detergents, proteins like bovine serum albumin (BSA), scavengers, etc.) or components that are necessary for detection of the newly synthesized DNA molecules such as, for example, fluorescent dyes and oligonucleotide probes. A reaction mixture is usually prepared at low temperatures at which enzymatic components are inactive, for example, by mixing the components on ice at ~0° C. When the reactions are ready, the mixtures can be heated to the desired reaction temperatures. In this aspect, the term "reaction temperature" refers to a temperature or a temperature range at which DNA synthesis is performed. In case of PCR reactions, it is usually taken as the lowest thermo-cycling temperature, commonly called the annealing temperature.

"dNTPs" is an abbreviation of a mixture of two or more of the four natural deoxynucleoside 5'-triphosphates that are useful to facilitate primer extension with a DNA polymerase and/or amplification. Respectively, the abbreviations "dATP," "dCTP," "dGTP," and "dTTP" correspond to the individual nucleotides. In some embodiments, the four dNTPs are present at equal concentrations. In other embodiments, the concentrations of the dNTPs are not all identical. In some embodiments, fewer than all four dNTPs are present. For example, only one dNTP may be present, or a pair-wise combination, or three of four dNTPs may be present in the mixture.

In some aspects, "amplification" and "amplifying" deoxyribonucleic acids, in general, refer to a procedure wherein multiple copies of DNA of interest are generated. The DNA amplification can be performed at a constant temperature using "isothermal amplification reactions." Examples of isothermal amplification reactions include, but are not limited to, Strand Displacement Amplification (SDA) (U.S. Pat. No. 5,270,184 to Walker, G. T., et al.; U.S. Pat. No. 6,214,587 to Dattagupta, N., et al.), Rolling Circle amplification (RCA) (U.S. Pat. No. 5,854,033 to Lizardi, P.), Loop Mediated Amplification (LMA) (U.S. Pat. No. 6,410,278 to Notomi, T. and Hase, T.), isothermal amplification using chimeric or composite RNA/DNA primers (U.S. Pat. No. 5,824,517 to Cleuziat, P. and Mandrand, B.; U.S. Pat. No. 6,251,639 to Kurn, N.), Nucleic Acid Sequence-Based Amplification (NASBA) (U.S. Pat. No. 6,063,603 to Davey, C. and Malek, L. T.), and many other methods.

"PCR" is an abbreviation of "polymerase chain reaction," an art-recognized nucleic acid amplification technology (e.g., U.S. Pat. Nos. 4,683,195 and 4,683,202 to Mullis, K. B.). Commonly used PCR protocol employs two oligonucleotide primers, one for each strand, designed such that extension of one primer provides a template for the other primer in the next PCR cycle. Generally, a PCR reaction consists of repetitions (cycles) of (i) a denaturation step that separates the strands of a double-stranded nucleic acid, followed by (ii) an annealing step, which allows primers to anneal to positions flanking a sequence of interest on a separated strand, and then (iii) an extension step that extends the primers in a 5' to 3' direction, thereby forming a nucleic acid fragment complementary to the target sequence. Each of the above steps may be conducted at a different temperature using an automated thermocycler. The PCR cycles can be repeated as often as desired resulting in an exponential accumulation of a target DNA fragment whose termini are usually defined by the 5'-ends of the primers used. Although conditions of PCR can vary in a broad range, a double-stranded target nucleic acid is usually denatured at a temperature of >90° C., primers are annealed at a temperature in the range of about 50-75° C., and the extension is preferably performed in a 72-75° C. temperature range. In PCR methods, the annealing and extension can be combined into one stage (i.e., using a single temperature). The term "PCR" encompasses its numerous derivatives such as "RT-PCR," "real-time PCR," "nested PCR," "quantitative PCR," "multiplexed PCR," "asymmetric PCR," and the like.

"Real-time detection" means an amplification reaction for which the amount of reaction product, i.e., target nucleic acid, is monitored as the reaction proceeds. Real-time detection is possible when all detection components are available during the amplification and the reaction composition and conditions support both stages of the reaction, the amplification and the detection.

As used herein, the term "kit" refers to any system for delivering materials. In the context of reaction assays, such delivery systems include elements allowing the storage, transport, or delivery of reaction components such as oligonucleotides, buffering components, additives, reaction enhancers, and the like in the appropriate containers from one location to another commonly provided with written instructions for performing the assay. Kits may include one or more enclosures or boxes containing the relevant reaction reagents and supporting materials. The kit may comprise two or more separate containers wherein each of those containers includes a portion of the total kit components. The containers may be delivered to the intended recipient together or separately.

In general, the term "design" in the context of the methods has broad meaning and in certain respects is equivalent to the term "selection." For example, the terms "primer design" and "aptamer design" can mean or encompass selection of a particular oligonucleotide structure including the nucleotide primary sequence and structural modifications (e.g., labels, modified nucleotides, linkers, etc.). In particular aspects, the terms "system design" and "assay design" relate to the selection of any, sometimes not necessarily to a particular, methods including all reaction conditions (e.g., temperature, salt, pH, enzymes, including the aptamer-modifying enzymes and DNA polymerase, oligonucleotide component concentrations, etc.), structural parameters (e.g., length and position of primers and probes, design of specialty sequences, etc.), and assay derivative forms (e.g., post-amplification, real time, immobilized, FRET detection schemes, etc.) chosen to amplify and/or to detect the nucleic acids of interest.

Reversible Blocking DNA Synthesis Activity of DNA Polymerases Using Aptamers.

Prior use of oligonucleotide aptamers during DNA synthesis have attempted to block DNA polymerase activity, preferably completely, at low temperatures, while releasing (activating) the DNA polymerase activity, preferably completely, at an elevated reaction temperature. It is difficult, however, to achieve complete 'block-and-release' formats using conventional aptamer-based methods (e.g., Yakimovich, O. Yu., et al., (2003); Jayasena, S. D. (1999); U.S. Pat. No. 5,693,502 to Gold, L. and Jayasena, S. D. (1997)). Effective blockage of DNA polymerase at low temperatures commonly leads to ineffective release of the enzyme at the elevated reaction temperature and vice versa. Aspects of the present invention provide a solution to this long-standing problem in the art. As in the conventional approaches cited above, the DNA polymerase activity is blocked or reduced in methods of the invention by the presence of an oligonucleotide aptamer that binds to the DNA polymerase, blocking the DNA synthesis activity of the DNA polymerase. Unlike prior art techniques, however, in methods of the invention, the aptamer-inactivated DNA polymerase is activated by providing to a DNA synthesis reaction mixture an endonuclease V enzyme activity that recognizes the oligonucleotide aptamer as a substrate and cleaves its structure. This cleavage reduces or eliminates the binding of the oligonucleotide aptamer to the DNA polymerase and thereby reactivates the DNA synthesis activity of the DNA polymerase.

In some embodiments of the invention, activation of an aptamer-inactivated DNA polymerase in a reaction mixture, comprising (i) a DNA polymerase, (ii) oligonucleotide aptamer in an amount effective to inhibit the DNA synthesis activity of the DNA polymerase, (iii) an endonuclease V aptamer-modifying enzyme and other components necessary for DNA synthesis, is facilitated using a reaction temperature that accelerates (or facilitates) both DNA polymerase and endonuclease V enzymatic activities. For example, the reaction mixture can be prepared at low temperature (first temperature) at which a DNA polymerase is effectively blocked by an aptamer and an aptamer-modifying enzyme, endonuclease V, has sufficiently reduced or preferably no activity (e.g., at 0° C.), and then the activation of the aptamer-inactivated DNA polymerase is facilitated by heating the reaction to a temperature (second temperature) that accelerates or facilitates the aptamer-modifying endonuclease V enzymatic activity. If necessary, a DNA polymerase can be activated by the endonuclease V enzyme(s) at any temperature below the reaction temperature for DNA synthesis. This can be applied, for example, when a particular endonuclease V enzyme is unstable at the reaction temperature for DNA synthesis, for example, due to denaturation. In this case, the DNA polymerase is first activated at an intermediate temperature wherein the endonuclease V is active and then heated to the reaction temperature to perform DNA synthesis.

In some aspects, the reaction mixture is created by addition of aqueous solution to one or more reaction components which are initially in a dried state as disclosed, for example, in U.S. Pat. No. 3,721,725 to Briggs, A. R. and Maxwell, T. J. (1973) (incorporated herein by reference). For example, in some methods of the invention for DNA amplification and detection, the aqueous solution can be a sample solution or solution that contains one or more polynucleotide templates for DNA synthesis whereas all other reaction components such as the DNA polymerase, aptamer, endonuclease V enzymatic activity, dNTPs, catalytic cofactors such as magnesium ($Mg^{2+}$) and/or manganese ($Mn^{2+}$) ion (e.g., provided as a chloride salt), buffering components, detergents, proteins like bovine serum albumin (BSA), scavengers, etc., are initially provided in a dry state.

In some aspects, DNA synthesis results in DNA amplification in the reaction mixture. The DNA amplification can be an isothermal amplification reaction, for example, as described in U.S. Pat. No. 5,270,184 to Walker, G. T., et al; U.S. Pat. No. 6,214,587 to Dattagupta, N., et al; U.S. Pat. No. 5,854,033 to Lizardi, P.; U.S. Pat. No. 6,410,278 to Notomi, T. and Hase, T.; U.S. Pat. No. 5,824,517 to Cleuziat, P. and Mandrand, B.; U.S. Pat. No. 6,251,639 to Kurn, N.; U.S. Pat. No. 6,063,603 to Davey, C. and Malek, L. T., and many other methods. In other aspects, the DNA amplification can be a PCR reaction (e.g., U.S. Pat. Nos. 4,683,195 and 4,683,202 to Mullis, K. B.). In methods of the invention, the DNA amplification is performed for detection as well as measuring an amount of a target DNA in the reaction mixture.

As has been established in the art (e.g., Yao, M., Kow, Y. W., 1997), a number of nucleotide modifications can be recognized by the endonuclease V enzymes to provide for the oligonucleotide cleavage. For example, an oligonucleotide aptamer that contains one or more deoxyuridine nucleotide(s) as described, for example, in Yao, M., Kow, Y. W., 1997, can be used in methods, compositions and kits of the present invention, such that contact of such aptamers with an endonuclease V enzymatic activity causes cleavage of the deoxyuridine-containing aptamer. However, the preferred modified nucleotide in aptamers is one or more deoxyinosine nucleotide(s). The endonuclease V enzymes of the present invention can cleave single-stranded and double-stranded oligonucleotides. Therefore the aptamers of the present invention can be both, single and double-stranded. In particular embodiments, the aptamers of the invention are stem-loop or hairpin-like molecules. Effective use of these two exemplary combinations (endonuclease V)+(deoxyinosine-incorporating aptamers) is illustrated in the Examples provided herein using, in particular, hairpin-like structures (FIGS. 2-7; as described in working Example 2 herein below). Deoxyinosine nucleotide can be located either in loop or stem fragments of the hairpin-like aptamers of the invention. Preferred locations of deoxyinosine modifications in aptamers of the present invention are described herein.

The oligonucleotide aptamers as well as oligonucleotide primers and probes can be prepared by any method of oligonucleotide synthesis selected by a person of ordinary skill in the art, such as methods that utilize (2-cyanoethyl)-(N,N-diisopropyl)]-phosphoramidites (Example 1). Protected nucleotides and derivatives, linkers, dyes, tails, solid supports, and other appropriate components can be prepared by methods of organic chemistry or obtained from market providers such as, for example, Glen Research and Biosearch Technologies. Suppliers such as Integrated DNA Technologies and Biosearch Technologies also offer oligonucleotide custom synthesis including numerous structural modifications such as deoxyinosine and deoxyuridine. In the methods of the invention, selection of an aptamer structure, including one or more deoxyinosine nucleotides, is intended to achieve (i) complete deactivation of the DNA polymerase at the initial reaction assembly temperature, (ii) complete or substantially complete (or as much as possible) deactivation of the DNA polymerase at the elevated reaction temperature for DNA synthesis, and (iii) substantially complete or complete (or as much as possible) reactivation of this enzyme at the DNA synthesis reaction temperature once the aptamer has been modified by the endonuclease V enzymatic activity. Generally, endonuclease V enzymes do not interfere with DNA synthesis (primer extension) or DNA amplification. The location and number of deoxyinosine nucleotides within an aptamer, as well as the rate and efficiency of the endonuclease V enzymes is preferably taken into consideration. Preference is given to deoxyinosine locations within an aptamer that have little or no negative effect on stability of the aptamer-DNA polymerase complex, but sufficiently disturb the structural integrity of the aptamer so that the cleaved aptamer does not bind to or inhibit the DNA polymerase. Results from aptamers containing deoxyinosine nucleotides (SEQ ID NOS:6-10 and 12-20) as the endonuclease V-recognition motif are illustrated in FIGS. 3, 5, 7, and 9. Surprisingly, even a single base modification at numerous locations showed excellent results in the exemplary assays.

According to the prior art (Yakimovich, O. Yu., et al. (2003); Jayasena, S. D. (1999); U.S. Pat. No. 5,693,502 to Gold, L. and Jayasena, S. D.), efficiency of hairpin-type aptamer binding to DNA polymerase is determined by (i) a loop segment, which is a substantially conservative sequence, and (ii) length of the stem duplex, which preferably needs to be ~19-20 base pairs or longer. In addition, the present inventors have found that the sequence of the stem fragment can be another important factor affecting the stability of an aptamer-polymerase complex. For example, the stem sequence of aptamers SEQ ID NOS:5 and 11 used in the present working Examples mostly comprises a $(AGT)_5$ nucleotide repeat (see FIGS. 2 and 4). However, these aptamers as well as many derivatives (SEQ ID NOS: 6-10 and 12-20) were very effective in blocking not only Taq (FIGS. 3, 5, and 7), but also many other DNA polymerases (FIG. 9). Out of six DNA polymerases investigated, only Bst polymerase (large fragment) was not inactivated by the aptamer SEQ ID NO:6. Analysis of FIG. 9 points to additional surprising results. First, regardless of the difference in reaction temperature, aptamer SEQ ID NO:6 blocked Phusion® polymerase much more efficiently at 65° C. than Taq polymerase at 60° C. According to additional surprising aspects of the invention, therefore, the best-blocking sequence of the aptamer hairpin duplex may be somewhat polymerase-specific. Second, the duplex sequence in an aptamer of the invention can be further optimized by base pair changes for even better polymerase blockage in each particular case. Third, using the sequence of aptamers SEQ ID NOS:5 and 11 as an origin, sequence optimization for strongest binding can be performed for every DNA polymerase known in the art, although for some DNA polymerases like Bst, optimization may require alterations in the loop segment of the aptamer as well as in the stem. In this sense, the present disclosure also provides methods of screening for more optimal aptamers for use in the disclosed methods.

Figure 7A:
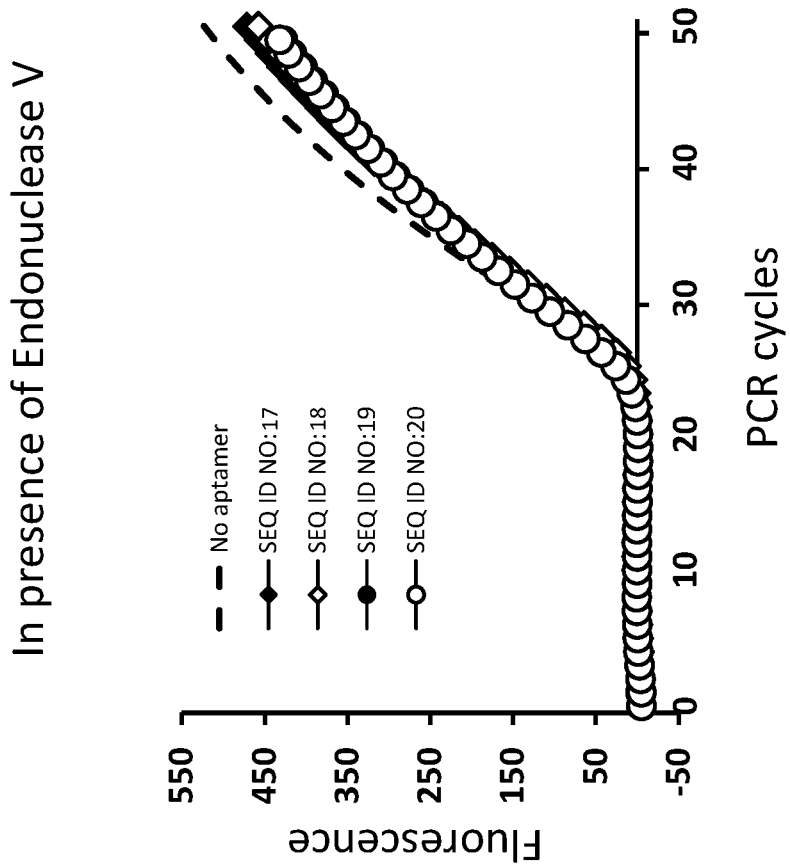
FIGS. 7A and 7B show, according to particular exemplary aspects, the results of fluorescence monitoring of reaction mixtures during PCR (real-time curves) in the presence of the individual aptamers listed in FIG. 6. Sequences of the amplified β2-microglobulin template, primers and 22-mer FRET probe used in the assays are as shown in FIG. 1. Dashed lines are real-time curves obtained in the absence of the aptamers. Experiments were conducted in the absence (FIG. 7A) or presence (FIG. 7B) of *T. maritima* endonuclease V. Experimental details are provided herein below under "Example 2."
Figure 7B:
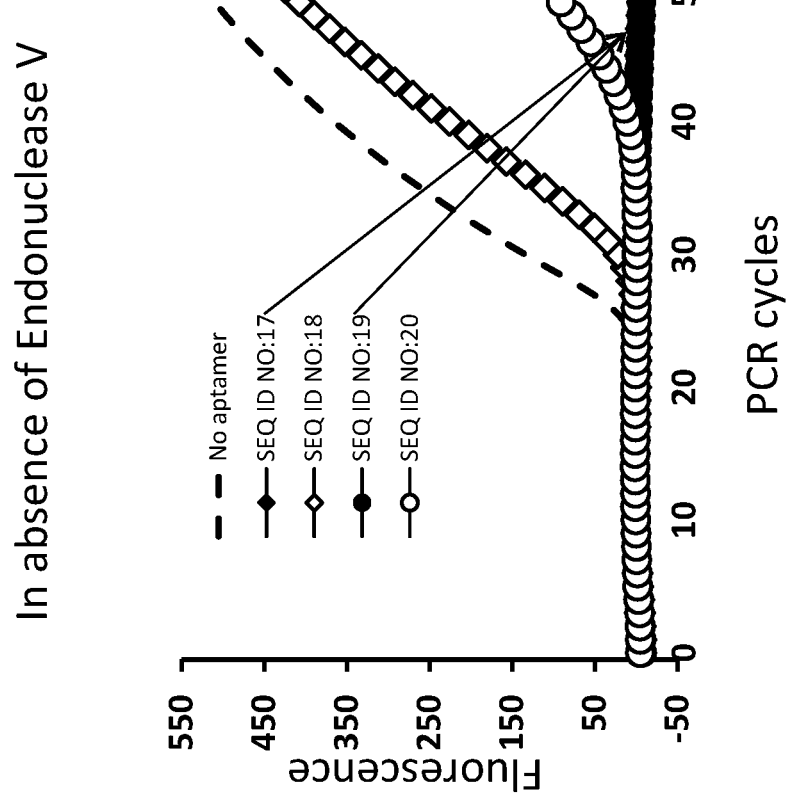

Aptamers of the invention, whether single-stranded or double-stranded, can contain any number of modified nucleotides, internal and external linker and moieties and other structural modifications as long as these modifications do not interfere with the DNA polymerase deactivation and then the activation processes during DNA synthesis. For example, if desirable in a specific assay, aptamers of the invention can include phosphorothioate bonds at their termini to protect the aptamers from the exonuclease hydrolysis (Skerra, A., 1992). Hairpin-type aptamers of the invention can also contain non-complementary 5' or 3' nucleotide sequences. Preference should be given to structural modifications that help to deactivate the DNA polymerase and do not adversely affect the endonuclease V enzyme activation reaction. Both loop and stem fragments can be modified in the hairpin-type aptamers. Although the loop segments described in Yakimovich, O. Yu., et al. (2003), Jayasena, S. D. (1999), and U.S. Pat. No. 5,693,502 to Gold, L. and Jayasena, S. D. contain conserved sequence motifs, the results in FIG. 7 (Example 2) herein show that deoxyinosine substitution(s) at certain loop positions have very little (SEQ ID NO:20) or no effect (SEQ ID NOS:17 and 19) on aptamer performance (FIG. 7).

Methods of the invention can be performed using one or more reaction temperatures wherein a DNA polymerase and endonuclease V express suitable activity. Specificity of DNA synthesis is usually increased at higher temperatures, and therefore thermostable enzymes are usually preferred. The upper level of the reaction temperature can be selected based on the DNA polymerase stability. In cases when an endonuclease V is not stable at a desired reaction temperature, the DNA polymerase activation can be initiated at a lower intermediate temperature wherein the endonuclease V is stable and active and then raised to the desired reaction temperature for DNA synthesis (primer extension). In some embodiments, a DNA polymerase is preferably first deactivated by contacting (e.g., by combining or mixing) with an aptamer before other reaction components of the DNA synthesis are added. Molar reaction concentration of an aptamer applied should be at least equal to the concentration of a DNA polymerase or preferably greater. Market providers commonly do not disclose the molar amount of the enzymes, therefore the precise excess of the aptamers over the DNA polymerases used in Examples provided herein was not known. However, the aptamers used in the Examples below were estimated to be present in a range of ~10-40 fold, or greater, molar excess relative to DNA polymerase. In some embodiments, the aptamer is present in a molar excess (ratio) over the DNA polymerases of at least ~5-fold, although the ratio can be higher or lower than 5-fold. The amounts of the enzymes, aptamers and other reaction components used in the reaction may be optimized and depend on many factors including, but not limited to selection of the particular enzymes, enzymatic activities at the reaction temperature, reaction temperature itself, nature of the aptamers, and their special endonuclease V recognition motifs (e.g., deoxyinosine or deoxyuridine, etc.) to provide for cleavage of the aptamers. Methods of the present invention can be particularly useful for so-called 'fast' PCR with a cycle time shorter than 20 seconds.

In certain embodiments, methods of the invention can be practiced using a kit comprising a DNA polymerase-binding oligonucleotide aptamer recognizable and modifiable by an endonuclease V enzymatic activity, and an endonuclease V enzyme activity to provide for specific cleavage of the aptamer. The kit can also include a DNA polymerase that is initially deactivated by the oligonucleotide aptamer. Alternatively, the kit can include, in addition to the endonuclease V enzyme activity, a complex of the DNA polymerase with the oligonucleotide aptamer, wherein the components of this complex are present at a specific and optimal molar ratio. As a matter of convenience, such a kit can include components allowing the storage, transport and other reaction components such as oligonucleotides, buffering components, additives, reaction enhancers, etc. The aptamers of the kits can be single-stranded or have a stem-loop structure, and they can incorporate one or more deoxyinosines or deoxyuridines. The kits can be used for the DNA synthesis, amplification as well as the detection of the amplified DNA fragments.

In some embodiments, the invention includes a reaction mixture comprising a DNA polymerase, an oligonucleotide aptamer that binds to the DNA polymerase and present in an amount effective to inhibit DNA synthesis activity of the DNA polymerase, an endonuclease V enzyme activity that is capable of cleaving the oligonucleotide aptamer to reduce or eliminate binding of the oligonucleotide aptamer to the DNA polymerase, and other reaction components necessary for DNA synthesis is also a subject of the present invention. In some embodiments, the reaction mixture can be assembled using concentrated stock solutions of one or more components, usually in water to provide the desired component concentration in the final mixture. Mixing is recommended to be performed at a low temperature (e.g., close to 0° C.) at which the enzymes, particularly endonuclease V enzymes, are inactive. Preferably, the reaction mixture should be used for DNA synthesis soon after preparation. Storage of a fully assembled reaction mixture is not recommended. However, reaction components including enzymes can retain activity for a long time (days, months, or even years) in a dried state. For example, in some embodiments of the invention, one or more of the components for forming a mixture of the invention can be provided in a dried form, such as dried beads as described, for example, in U.S. Pat. No. 3,721,725 to Briggs, A. R. and Maxwell, T. J. (1973), including (but not limited to) DNA polymerase, oligonucleotide aptamer, and endonuclease V enzyme activity such that one or more of the components is prepared in a form of dried beads as described, for example, in U.S. Pat. No. 3,721,725 to Briggs, A. R. and Maxwell, T. J. (1973). In some embodiments, the mixture comprises DNA polymerase, an oligonucleotide aptamer that binds to the DNA polymerase and present in an amount effective to inhibit DNA synthesis activity of the DNA polymerase, and an endonuclease V enzyme activity that is capable of cleaving the oligonucleotide aptamer to reduce or eliminate binding of the oligonucleotide aptamer to the DNA polymerase, which are mixed together in a dried form.

EXAMPLE 1

Synthesis of Aptamers, Primers and Fluorescent Probes

Figure 8:
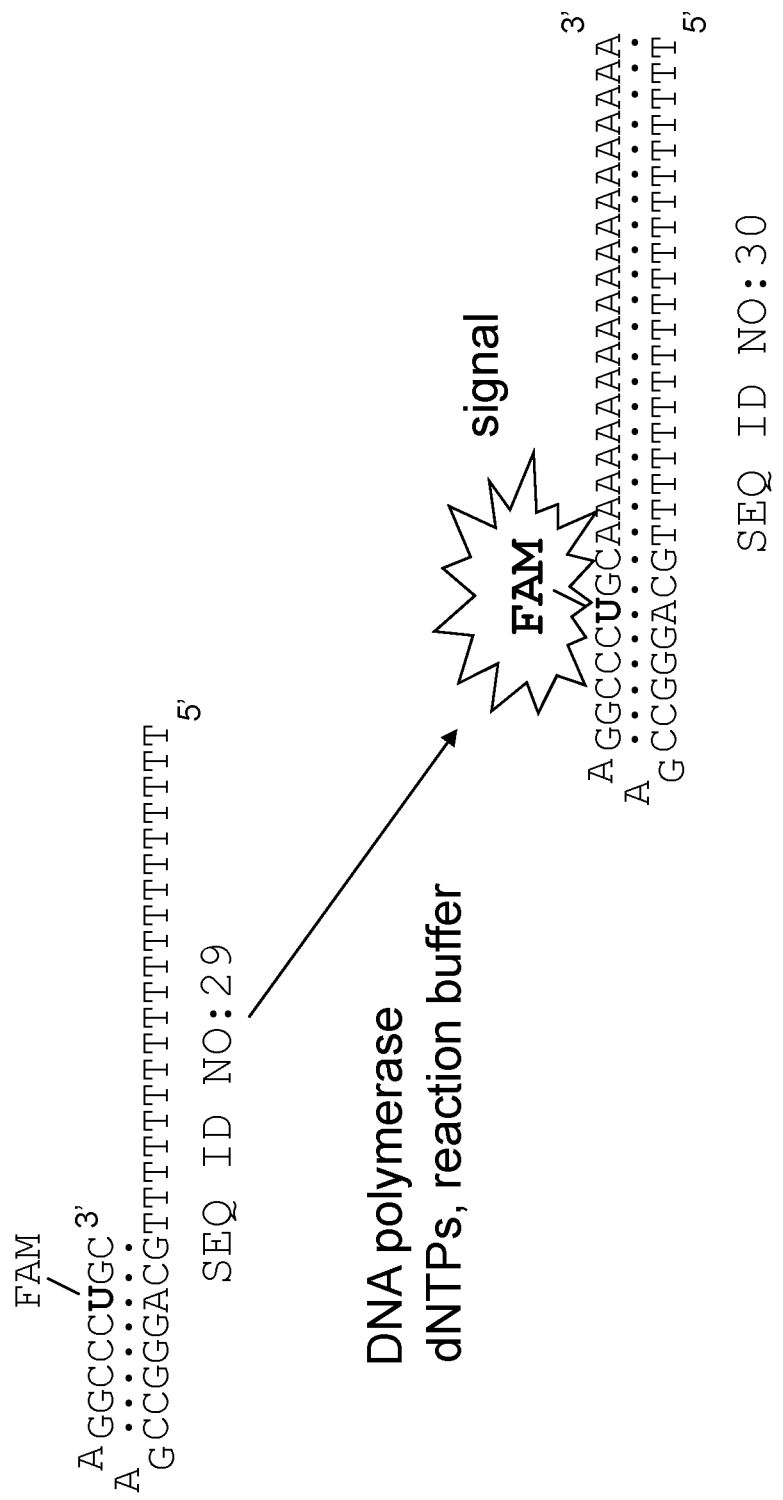
FIG. 8 shows, according to particular exemplary aspects, a reaction scheme used in the assays of FIGS. 9A through 9F to detect and measure DNA polymerase activity. The depicted hairpin-like fluorescent probe SEQ ID NO:29 was designed to have a G/C-rich stem in the duplex segment and a 5'- . . . GAA . . . hairpin-stabilizing loop to provide for use at elevated temperatures (e.g., up to 60-65° C.) (e.g., see Yoshizawa S., et al, 1994). Extension of this hairpin-like probe in a reaction buffer in the presence of deoxyribonucleoside 5'-triphosphates (dNTPs) and a DNA polymerase results in a fluorescent signal that directly correlates with the polymerase activity in the reaction.

Standard phosphoramidites, including modified nucleotide analogs such as deoxyinosine phosphoramidite (Catalog Number: 10-1040-xx), solid supports and reagents to perform solid support oligonucleotide synthesis, were purchased from Glen Research. A 0.25 M 5-ethylthio-1H-tetrazole solution was used as a coupling agent. Oligonucleotides were synthesized either on ABI394 DNA synthesizer (Applied Biosystems) or MerMaid 6 DNA synthesizer (BioAutomation Corporation) using protocols recommended by the manufacturers for 0.2 μmole synthesis scales. Fluorescein (FAM) conjugated to 5-position of deoxyribouridine (U) of probe SEQ ID NO:29 (FIG. 8) was introduced to the hairpin during oligonucleotide synthesis using 5'-dimethoxytrityloxy-5-[N-((3',6'-dipivaloyl fluoresceinyl)-aminohexyl)-3-acrylimido]-2'-deoxyribouridine-3'-[(2-cyanoethyl)-(N,N-diisopropyl)]-phosphoramidite (Glen Research, Catalog Number: 10-1056-xx). A 6-fluorescein reporting dye was incorporated onto the 5'-end, and a BHQ1 quencher was introduced to the 3'-end of probe SEQ ID NO:3 (FIG. 1) using respective phosphoramidite and CPG from Biosearch Technologies (Catalog numbers: BNS-5025 and BG1-5041G). After the automated synthesis, oligonucleotides were deprotected in aqueous 30% ammonia solution by incubation for 12 hours at 55° C. or 2 hours at 70° C.

Tri-ON oligonucleotides were purified by HPLC on a reverse phase C18 column (LUNA 5 μm, 100 A, 250×4.6 mm, Phenomenex Inc.) using gradient of acetonitrile in 0.1 M triethyl ammonium acetate (pH 8.0) or carbonate (pH 8.5) buffer with flow rate of 1 ml/min. A gradient profile including washing stage 0→14% (10 sec), 14→45% (23 min), 45→90% (10 min), 90→90% (5 min), 90→0% (30 sec), 0→0% (7 min) was applied for purification of all Tri-ON oligonucleotides. The product containing fractions were dried down in vacuum (SPD 1010 SpeedVac, TermoSavant) and trityl groups were removed by treatment in 80% aqueous acetic acid at room temperature for 40-60 min. After addition to the detritylation reaction (100 μl) of 20 μl sodium acetate (3 M), the oligonucleotide components were precipitated in alcohol (1.5 ml), centrifuged, washed with alcohol and dried down. Concentration of the oligonucleotide components was determined based on the optical density at 260 nm and the extinction coefficients calculated for individual oligonucleotides using on-line OligoAnalyzer 3.0 software provided by Integrated DNA Technologies. Based on the measurements, convenient stock solutions in water were prepared and stored at −20° C. for further use. The purity of all prepared oligonucleotide components was confirmed by analytical 8-20% PAAG electrophoresis, reverse phase HPLC and by spectroscopy on Cary 4000 UV-VIS spectrophotometer equipped with Cary WinUV software, Bio Package 3.0 (Varian, Inc.).

EXAMPLE 2

Application of Deoxyinosine-Containing Aptamers to Control Polymerase Activity of Taq Polymerase This working example shows application of deoxyinosine-containing aptamers to control activity of Taq polymerase during PCR.

Figure 3B:
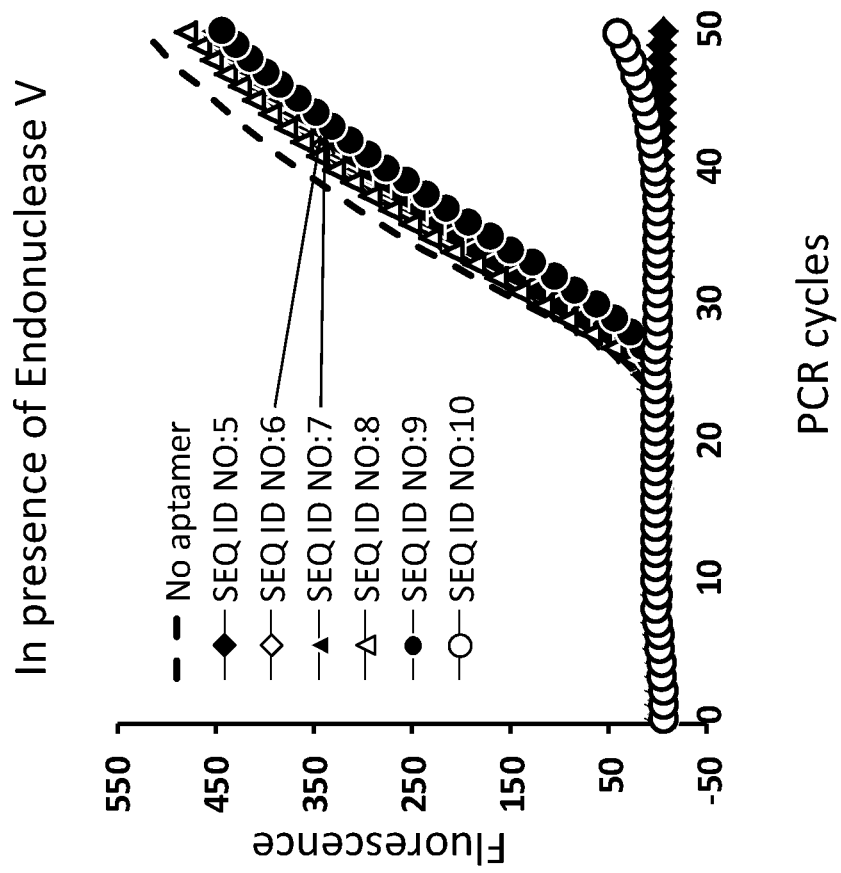
FIGS. 3A and 3B show, according to particular exemplary aspects, the results of fluorescence monitoring of reaction mixtures during PCR (real-time curves) in the presence of the individual aptamers listed in FIG. 2. Sequences of the amplified β2-microglobulin template, primers and 22-mer FRET probe used in these PCR assays are as shown in FIG. 1. Dashed lines are real-time curves obtained in the absence of any aptamer. Experiments were conducted in the absence (FIG. 3A) or presence (FIG. 3B) of *T. maritima* endonuclease V. Experimental details are provided below in "Example 2."
Figure 3A:
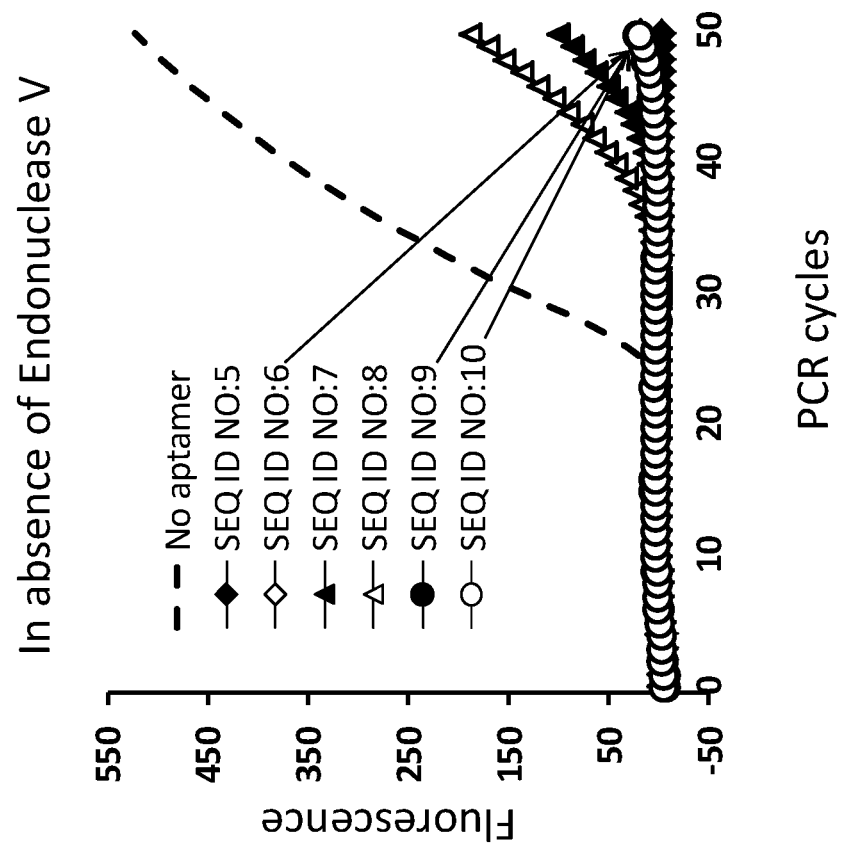
Figure 5B:
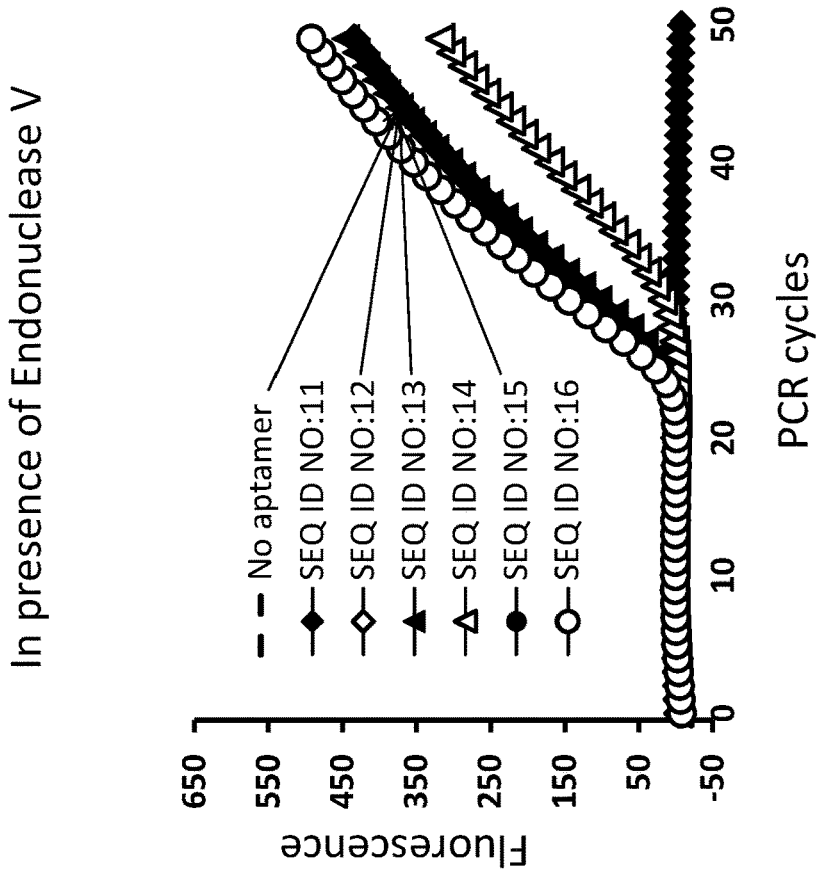
FIGS. 5A and 5B show, according to particular exemplary aspects, the results of fluorescence monitoring of reaction mixtures during PCR (real-time curves) in the presence of the individual aptamers listed in FIG. 4. Sequences of the amplified β2-microglobulin template, primers and 22-mer FRET probe used in the assays are as shown in FIG. 1. Dashed lines are real-time curves obtained in the absence of any aptamer. Experiments were conducted in the absence (FIG. 5A) or presence (FIG. 5B) of *T. maritima* endonuclease V. Experimental details are provided herein below under "Example 2."
Figure 5A:
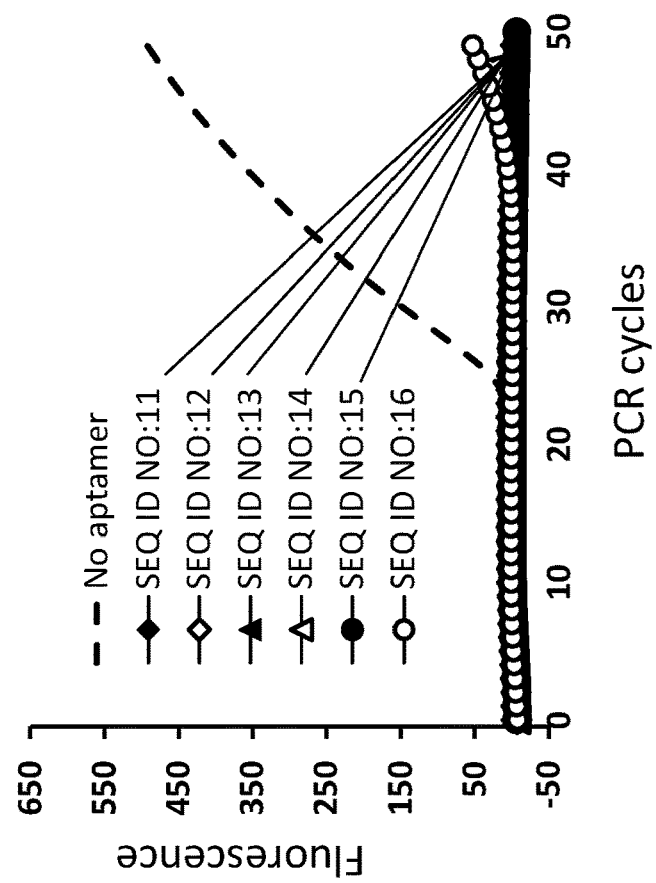

For the results shown in FIGS. 3, 5, and 7, reaction mixtures (25 μL) were prepared on ice by mixing corresponding stock solutions to provide 200 nM forward primer (FIG. 1, SEQ ID NO:1), 300 nM reverse primer (SEQ ID NO:2), 200 nM FRET probe (SEQ ID NO:3), 0.02 U/μL Taq DNA polymerase (GenScript cat no: E00007), dNTPs (200 μM each), bovine serum albumin (0.1 μg/μL), 100 ng of human genomic DNA (GenScript cat no: M00094) and, when present, one of the aptamers SEQ ID NOS:5-20 (20 nM) in 5 mM MgCl$_2$, 50 mM KCl, 20 mM Tris-HCl (pH 8.0). The reaction tubes were quickly transferred into Smart-Cycler instrument (Cepheid Corporation) and temperature cycling initiated. The PCR time/temperature profile comprised initial incubation at 95° C. for 15 seconds followed by 50 cycles of incubation at 95° C. for 1 second and then at 60° C. for 20 seconds. The reaction fluorescence was measured in every PCR cycle during the annealing/extension stage (60° C.) and the results are shown in FIGS. 3, 5, and 7. Each fluorescence curve is an average of four identical reactions. Initial background fluorescence was subtracted by the instrument software.

Figure 2:
FIG. 2 shows, according to particular exemplary aspects, structures of stem-loop deoxyribonucleotide aptamers used in exemplary 5'-nuclease PCR assays of the present invention from which exemplary results are shown in FIGS. 3A and 3B. The symbol "I" indicates the presence of deoxyriboinosine nucleotides in aptamers SEQ ID NOS:6-10 that were used in experiments with endonuclease V. Arrows point to the expected endonuclease V cleavage positions.
Figure 2:
Figure 2:
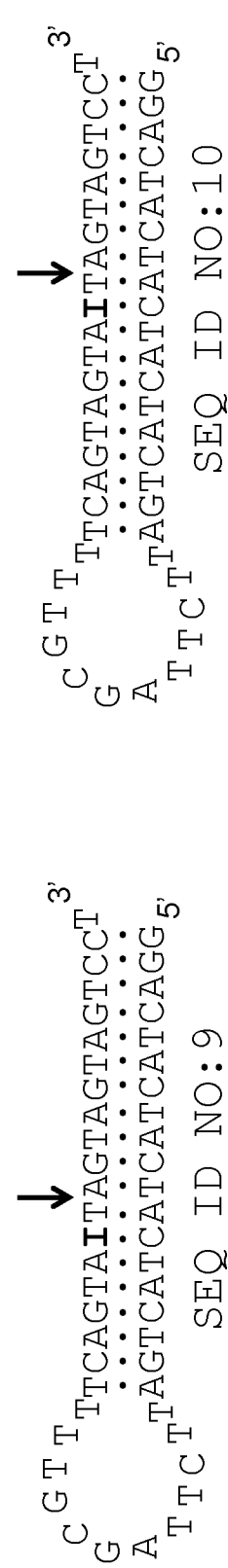
Figure 4:
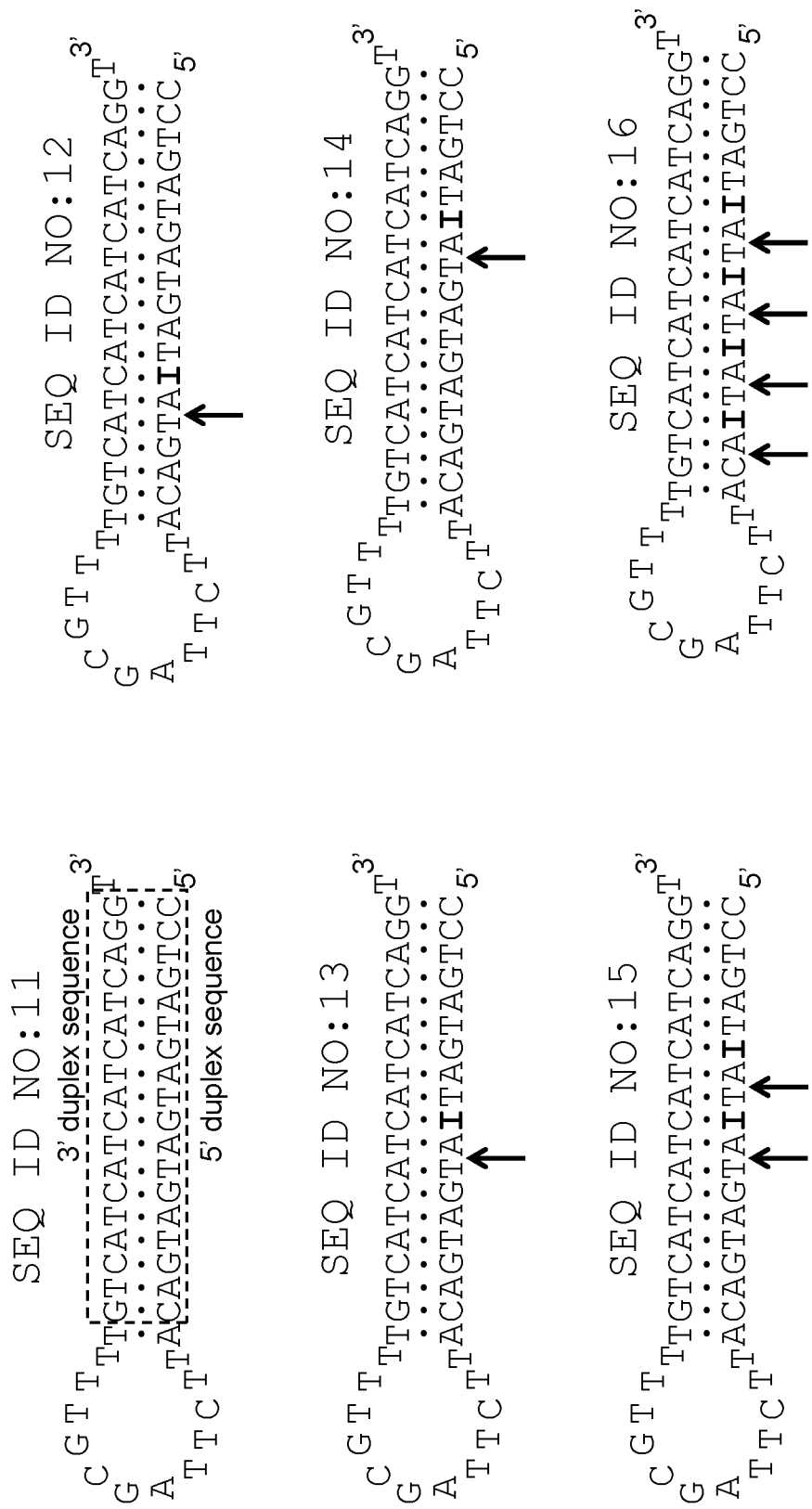
FIG. 4 shows, according to particular exemplary aspects, structures of additional stem-loop deoxyribonucleotide aptamers used in the 5'-nuclease PCR assays from which exemplary results are shown in FIGS. 5A and 5B. Unmodified aptamer SEQ ID NO:11 has the same natural base composition as unmodified aptamer SEQ ID NO:5 of FIG. 2, but was produced by exchanging the upper and lower sequences of SEQ ID NO:5 within the double-stranded stem portion delineated by the dashed box. This design approach provided further elucidation of the effect of guanosine-to-inosine substitutions in the 5' duplex sequence of aptamers SEQ ID NOS:12-16, which are modified versions of SEQ ID NO:11 (the symbol "I" means a deoxyriboinosine nucleotide). Arrows point to endonuclease V cleavage positions.
Figure 6:
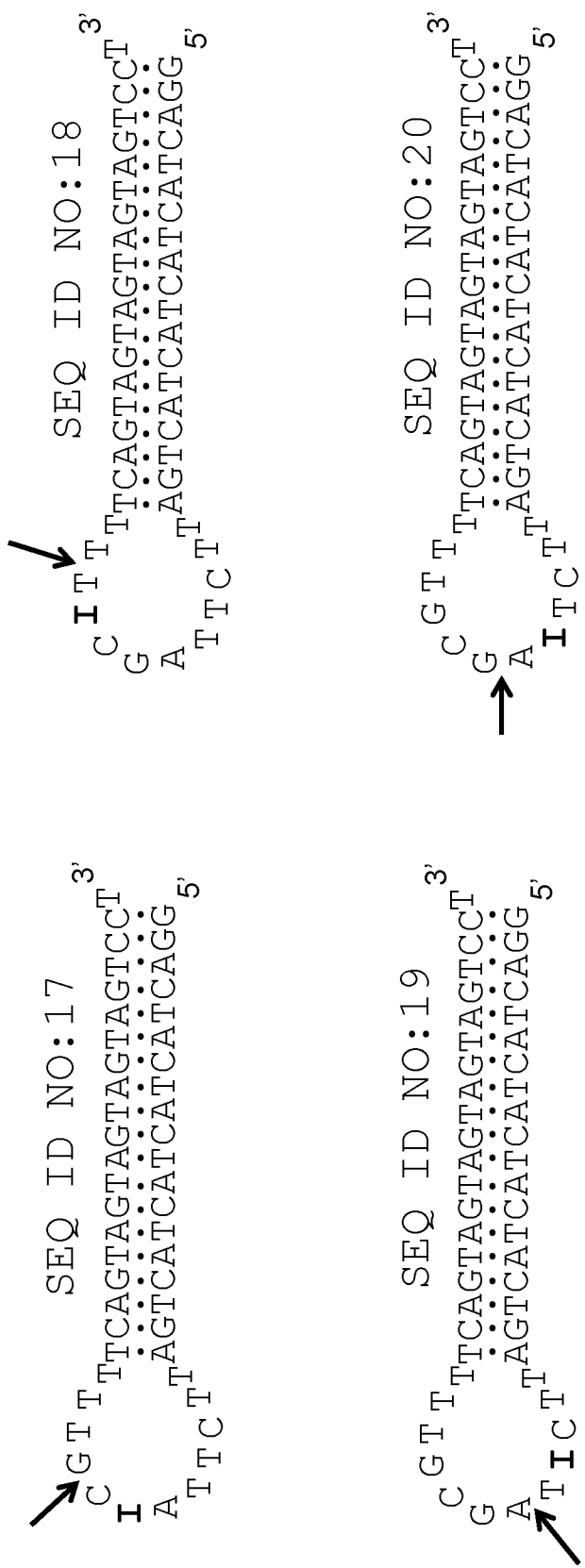
FIG. 6 shows, according to particular exemplary aspects, structures of four additional stem-loop deoxyribonucleotide aptamers SEQ ID NOS:17-20 that are derivatives of the aptamer SEQ ID NO:5 of FIG. 2 incorporating deoxyinosine nucleotide (symbol "I") in the loop portion at various positions. These aptamers were used in the 5'-nuclease PCR assays of FIGS. 7A and 7B. Arrows point to the anticipated endonuclease V cleavage positions.

The reaction conditions used to generate the fluorescence profiles shown in FIGS. 3, 5, and 7 were identical except for the presence or absence of endonuclease V enzymatic activity and the presence or absence of different oligonucleotides as potential inhibitors of polymerase activity. PCR reactions were performed either in the absence (left diagram of each figure) or presence (right diagram) of *T. maritima* endonuclease V (0.04 U/μL, Fisher Scientific cat no: FEREN0141) in the reaction mixtures. Structures of the oligonucleotide aptamers used in the experiments of FIGS. 3, 5, and 7 are shown in FIGS. 2, 4, and 6, respectively.

In summary of this working Example, the real-time curves shown in FIGS. 3 and 5 show that unmodified aptamer SEQ ID NO:5 and it structural analog SEQ ID NO:11 effectively block Taq polymerase activity during PCR and are not affected by the presence of endonuclease V activity in the reaction mixture. Analysis of the real-time PCR curves in FIGS. 3 and 5 leads to the following conclusions. Virtually ideal results of DNA polymerase inactivation-activation were obtained for the aptamers SEQ ID NOS:6, 9, 12, and 13, wherein endonuclease V cleavage takes place nearby the duplex center, but closer to the loop fragment. However, when the deoxyinosine nucleotide is too close to the loop, the corresponding aptamer SEQ ID NO:7 becomes less effective in blockage of the DNA polymerase, likely due to profound destabilization of the aptamer duplex segment adjacent to the loop. When the endonuclease V cleavage site is located closer to the aptamer duplex 3' or 5' ends, as in the cases of aptamers SEQ ID NOS:10 and 14, the truncated hairpin products were likely to retain thermal stability and duplex length that is sufficient for blockage of the Taq DNA polymerase during PCR. Moreover, the truncated hairpin product resulted after the cleavage of aptamer SEQ ID NO:10 can be extended by the DNA polymerase thereby restoring the original aptamer duplex structure. This may explain the extreme "no activation" result observed for SEQ ID NO:10 (FIG. 3B). Incorporation of more than one deoxyinosine modifications into aptamer duplex (aptamers SEQ ID NOS:8, 15, and 16) can be applied, but it is generally unnecessary. Furthermore, increase in the number of I-C base pairs usually leads to destabilization of the aptamer duplex and thus negatively affects ability of the aptamers to inactivate the DNA polymerase (e.g., aptamers SEQ ID NOS:8 and 16).

Regarding ability of the hairpin-like aptamers to inactivate Taq DNA polymerase, the loop sequence 5'TTCTTAGCGTTT3' (SEQ ID NO:21) is known to be highly conserved (e.g. Yakimovich, O. Yu., et al. (2003), Jayasena, S. D. (1999), and U.S. Pat. No. 5,693,502 to Gold, L. and Jayasena, S. D.). Nevertheless, a number of the nucleotide substitutions by deoxyinosine in the aptamers SEQ ID NOS:17-20 shown in FIG. 6 was investigated, and the real-time PCR results are provided in FIG. 7. Significant difference in properties was found for the aptamers SEQ ID NOS:17 and 18. Both aptamers completely lose capability to block Taq DNA polymerase after endonuclease V cleavage. However, in the absence of such cleavage, the aptamer SEQ ID NO:18 showed very weak inactivation of the DNA polymerase whereas the aptamer SEQ ID NO:17 appeared to be ideal in the polymerase inactivation-activation performance. The aptamers SEQ ID NOS:17 and 18 represent a homologous guanine-to-hypoxanthine purine substitution. The most surprising results were obtained for the aptamers SEQ ID NOS:19 and 20 representing nonhomologous (pyrimidine-purine) thymine-hypoxanthine base alteration within the highly conservative loop sequence. Both aptamers inactivated the DNA polymerase (FIG. 7A), although the aptamer SEQ ID NO:20 was somewhat less effective, whereas treatment of the PCR reactions with endonuclease V completely restored Taq DNA polymerase activity. In conclusion, investigation of the deoxyinosine substitutions within the aptamer loop sequences allowed identification of at least three exemplary nucleotide locations that can be used in embodiments of the present invention. For example, the loop sequences 5'-TTCITAGCGTTT-3' (SEQ ID NO:22), 5'-TTCTIAGCGTTT-3' (SEQ ID NO:23), 5'-TTCTTAICGTTT-3' (SEQ ID NO:24), 5'-TTCIIAGCGTTT-3' (SEQ ID NO:25), 5'-TTCITAICGTTT-3' (SEQ ID NO:26), 5'-TTCTIAICGTTT-3' (SEQ ID NO:27), and 5'-TTCIITAICGTTT-3' (SEQ ID NO:28) incorporating 1, 2, or 3 deoxyinosine nucleotides can be used in design of the hairpin-like aptamers for the methods of the present invention.

EXAMPLE 3

Kinetics of Activation by Endonuclease V of Various DNA Polymerases Initially Blocked by Deoxyinosine-Containing Aptamer This working example shows the kinetics of activation by endonuclease V of Taq (GenScript cat no: E00007), Q5® (New England Biolabs cat no: M0491S), Vent® (New England Biolabs cat no: M0254S), Deep Vent® (New England Biolabs cat no: M0258S), Bst large fragment (New England Biolabs cat no: M0275S), and Phusion® (New England Biolabs cat no: M0530S) DNA polymerases initially blocked by a deoxyinosine-containing aptamers.

For FIG. 9, reaction mixtures (25 μL) were prepared on ice by mixing corresponding stock solutions to provide self-priming hairpin SEQ ID NO:29 (200 nM, FIG. 8), a DNA polymerase (0.008 U/μL), dNTPs (200 μM each), bovine serum albumin (0.1 μg/μL) and, when present, the aptamer SEQ ID NO:6 (80 nM, FIG. 2) and *T. maritima* endonuclease V (0.02 U/μL, Fisher Scientific cat no: FEREN0141) in 5 mM MgCl$_2$, 50 mM KCl, 20 mM Tris-HCl (pH 8.0). During preparation of the reaction mixture, the self-priming hairpin (SEQ ID NO:29) and endonuclease V were always added last to a premixed solution. Then the reaction tubes were transferred into a SmartCycler instrument (Cepheid Corporation) and heated to 60 or 65° C. as indicated for each fluorescence profile in FIG. 9. The reaction fluorescence was monitored every 7 seconds. The plotted curves are the averages of four paralleled identical reactions. Initial background fluorescence was subtracted.

The results of FIG. 9 show that not only Taq polymerase, but also many other DNA polymerases can be inactivated and then activated using endonuclease V-cleavable aptamers of the present invention. Only one of six investigated exemplary DNA polymerases, particularly Bst DNA polymerase, was not inactivated by aptamer SEQ ID NO:6.

Other DNA polymerases showed a 'delayed' activation in the presence of the endonuclease V before the DNA synthesis activity was restored.

References cited, and incorporated by reference herein for their respective teachings:

Cleuziat, P., and Mandrand, B., "Method for amplifying nucleic acid sequences by strand displacement using DNA/RNA chimeric primers," 1998, U.S. Pat. No. 5,824,517.

Dattagupta, N., Stull, P. D., Spingola, M., and Kacian, D. L., "Isothermal strand displacement nucleic acid amplification," 2001, U.S. Pat. No. 6,214,587.

Davey, C., and Malek, L. T., "Nucleic acid amplification process," 2000, U.S. Pat. No. 6,063,603.

Eckstein, F., ed., (1991) *Oligonucleotides and Analogs: A Practical Approach*. Oxford University Press, New York.

Hedgpeth, J., Afonina, I. A., Kutyavin, I. V., Lukhtanov, E. A., Belousov, E. S., and Meyer, Jr., R. B., "Hybridization and mismatch discrimination using oligonucleotides conjugated to minor groove binders," 2010, U.S. Pat. No. 7,794,945.

Gait, M. J., ed., (1984) *Oligonucleotide Synthesis: A Practical Approach*, IRL Practical Approach Series, IRL Press, Oxford.

Gold, L. and Jayasena, S. D., "Nucleic acid ligand inhibitors to DNA polymerase," 1997, U.S. Pat. No. 5,693,502.

Jayasena, S. D., "Aptamers: An emerging class of molecules that rival antibodies in diagnostics," *Clinical Chemistry* 45:1628-1650, 1999.

Kornberg, A., and Baker, T. (1992) *DNA Replication*, Second Edition, W. H. Freeman and Company, New York.

Kurn, N., "Methods and compositions for linear isothermal amplification of polynucleotide sequences, using a RNA-DNA composite primer," 2001, U.S. Pat. No. 6,251,639.

Kutyavin, I. V., and Lukhtanov, E. A., Gamper, H. B., Meyer, Jr., R. B., "Covalently linked oligonucleotide minor grove binder conjugates," 1998, U.S. Pat. No. 5,801,155.

Kutyavin, I. V., "Accelerated cascade amplification (ACA) of nucleic acids comprising strand and sequence specific DNA nicking," 2012, U.S. Pat. No. 8,143,006.

Kutyavin, I. V., "Use of base-modified deoxynucleoside triphosphates to improve nucleic acid detection," 2013, U.S. Pat. No. 8,349,556.

Lehninger, A. L. (1975) *Biochemistry*, 2nd edition. New York, Worth Publishers, Inc.

Lizardi, P., "Rolling circle replication reporter systems," 1998, U.S. Pat. No. 5,854,033.

Martin, F. H., and Castro, M. M., "Base pairing involving deoxyinosine: implications for probe design," *Nucleic Acids Res.* 13:8927-8938, 1985.

Meyer, Jr., R. B., Afonina, I. A., and Kutyavin, I. V., "Oligonucleotides containing pyrazolo[3,4-D]pyrimidines for hybridization and mismatch discrimination," 2000, U.S. Pat. No. 6,127,121.

Mullis, K. B., "Process for amplifying nucleic acid sequences," 1987, U.S. Pat. No. 4,683,202.

Mullis, K. B., Erlich, H. A., Arnheim, N., Horn, G. T., Saiki, R. K., and Scharf, S. J., "Process for amplifying, detecting, and/or -cloning nucleic acid sequences," 1987, U.S. Pat. No. 4,683,195.

Notomi, T., and Hase, T., "Process for synthesizing nucleic acid," 2002, U.S. Pat. No. 6,410,278.

Paul, N., Shum, J., and Le, T. (2010), Hot start PCR. In King N. (ed.), *RT-PCR Protocols: Second Edition*. Methods in Molecular Biology, Springer Science+Business Media, LLC, V.630:301-318.

Sambrook, J., et al. (1989), *Molecular Cloning: A Laboratory Manual*, 2nd Edition. Cold Spring Harbor Lab. Cold Spring Harbor, NY.

Skerra, A., "Phosphorothioate primers improve the amplification of DNA sequences by DNA polymerases with proofreading activity," *Nucleic Acids Res.* 20:3551-3554, 1992.

Walker, G. T., Little, M. C., and Nadeau, J. G., "Nucleic acid target generation," 1993, U.S. Pat. No. 5,270,184.

Yakimovich, O. Yu., Alekseev, Ya. I., Maksimenko, A. V., Voronina, O. L., and Lunin, V. G., "Influence of DNA aptamer structure on the specificity of Binding to Taq DNA polymerase," *Biochemistry (Moscow)* 68:228-235, 2003.

Yao, M., and Kow, Y. W., "Further Characterization of *Escherichia coli* Endonuclease V. Mechanism of Recognition for Deoxyinosine, Deoxyuridine, and Base Mismatches in DNA," *J. Biol. Chem.* 272:30774-30779, 1997.

Yoshizawa, S., Ueda, T., Ishido, Y., Miura, K., Watanabe, K., and Hirao, I., "Nuclease resistance of an extraordinarily thermostable mini-hairpin DNA fragment, d(GCGAAGC) and its application to in vitro protein synthesis," *Nucleic Acids Res.* 22:2217-2221, 1994.

The invention claimed is:

1. An oligonucleotide aptamer, comprising a nucleic acid sequence that forms a hairpin structure, having a stem and a loop portion, that binds to a DNA polymerase, wherein the stem and/or the loop portion comprises one or more deoxyinosine nucleotides, and wherein the loop portion comprises a nucleotide sequence 5'-TTCTTAGCGTTT-3' (SEQ ID NO:21) that may be substituted with deoxyinosine at one or more of positions 4, 5, and 7.

2. The oligonucleotide aptamer of claim 1, wherein the loop portion comprises the nucleotide sequence 5'-TTCTTAGCGTTT-3' (SEQ ID NO:21).

3. The oligonucleotide aptamer of claim 1, wherein the one or more deoxyinosine nucleotides are located in the stem segment of the stem-loop structure.

4. The oligonucleotide aptamer of claim 1, wherein the one or more deoxyinosine nucleotides are located in the loop segment of the stem-loop structure.

5. The oligonucleotide aptamer of claim 4, wherein the loop of the stem-loop structure, comprises a nucleotide sequence selected from the group consisting of 5'-TTCI-TAGCGTTT-3' (SEQ ID NO:22), 5'-TTCTIAGCGTTT-3' (SEQ ID NO:23), 5'-TTCTTAICGTTT-3' (SEQ ID NO:24), 5'-TTCIIAGCGTTT-3' (SEQ ID NO:25), 5'-TTCITA-ICGTTT-3' (SEQ ID NO:26), 5'-TTCTIAICGTTT-3' (SEQ ID NO:27), and 5'-TTCIITAICGTTT-3' (SEQ ID NO:28).

6. The oligonucleotide aptamer of claim 5, wherein the loop of the stem-loop structure comprises one of the nucleotide sequences 5'-TTCITAGCGTTT-3' (SEQ ID NO:22), 5'-TTCTIAGCGTTT-3' (SEQ ID NO:23), or 5'-TTCTTA-ICGTTT-3' (SEQ ID NO:24).

7. The oligonucleotide aptamer of claim 1, wherein the one or more deoxyinosine nucleotides renders the oligonucleotide aptamer cleavable by an endonuclease V enzymatic activity.

8. The oligonucleotide aptamer of claim 7, wherein endonuclease V enzymatic activity comprises *Thermotoga maritima* endonuclease V enzymatic activity.

9. The oligonucleotide aptamer of claim 1, complexed with a DNA polymerase.

* * * * *

SEQUENCE LISTING

```
<160> NUMBER OF SEQ ID NOS: 30

<210> SEQ ID NO 1
<211> LENGTH: 21
<212> TYPE: DNA
<213> ORGANISM: Artificial Sequence
<220> FEATURE:
<223> OTHER INFORMATION: forward primer

<400> SEQUENCE: 1
gcattcctga agctgacagc a                                                   21

<210> SEQ ID NO 2
<211> LENGTH: 24
<212> TYPE: DNA
<213> ORGANISM: Artificial Sequence
<220> FEATURE:
<223> OTHER INFORMATION: reverse primer
<220> FEATURE:
```

```
<400> SEQUENCE: 2
ctccaggcca gaaagagaga gtag                                          24

<210> SEQ ID NO 3
<211> LENGTH: 22
<212> TYPE: DNA
<213> ORGANISM: Artificial Sequence
<220> FEATURE:
<223> OTHER INFORMATION: oligonucleotide probe sequence
<220> FEATURE:
<221> NAME/KEY: misc_feature
<222> LOCATION: (1)...(1)
<223> OTHER INFORMATION: 5'-FAM-labelled FRET prob
<220> FEATURE:
<221> NAME/KEY: misc_feature
<222> LOCATION: (22)...(22)
<223> OTHER INFORMATION: 3'-BHQ1-labelled FRET probe

<400> SEQUENCE: 3
ccgtggcctt agctgtgctc gc                                            22

<210> SEQ ID NO 4
<211> LENGTH: 91
<212> TYPE: DNA
<213> ORGANISM: Homo sapiens
<220> FEATURE:
<221> NAME/KEY: gene
<222> LOCATION: (0)...(0)
<223> OTHER INFORMATION: Human _2-microglobulin target sequence

<400> SEQUENCE: 4
ggcattcctg aagctgacag cattcgggcc gagatgtctc gctccgtggc cttagctgtg   60
ctcgcgctac tctctctttc tggcctggag g                                  91

<210> SEQ ID NO 5
<211> LENGTH: 51
<212> TYPE: DNA
<213> ORGANISM: Artificial Sequence
<220> FEATURE:
<223> OTHER INFORMATION: hairpin loop oligonucleotide aptamer sequence

<400> SEQUENCE: 5
ggactactac tactactgat tcttagcgtt ttcagtagta gtagtagtcc t             51

<210> SEQ ID NO 6
<211> LENGTH: 51
<212> TYPE: DNA
<213> ORGANISM: Artificial Sequence
<220> FEATURE:
<223> OTHER INFORMATION: hairpin loop oligonucleotide aptamer sequence
<220> FEATURE:
<221> NAME/KEY: modified_base
<222> LOCATION: (35)...(35)
<223> OTHER INFORMATION: I
<220> FEATURE:
<221> NAME/KEY: misc_feature
<222> LOCATION: (35)...(35)
<223> OTHER INFORMATION: Inosine at position 35

<400> SEQUENCE: 6
ggactactac tactactgat tcttagcgtt ttcantagta gtagtagtcc t             51

<210> SEQ ID NO 7
<211> LENGTH: 51
<212> TYPE: DNA
<213> ORGANISM: Artificial Sequence
<220> FEATURE:
<223> OTHER INFORMATION: hairpin loop oligonucleotide aptamer sequence
```

```
<220> FEATURE:
<221> NAME/KEY: modified_base
<222> LOCATION: (18)...(18)
<223> OTHER INFORMATION: I
<220> FEATURE:
<221> NAME/KEY: misc_feature
<222> LOCATION: (18)...(18)
<223> OTHER INFORMATION: Inosine at position 18

<400> SEQUENCE: 7
ggactactac tactactnat tcttagcgtt ttcagtagta gtagtagtcc t          51

<210> SEQ ID NO 8
<211> LENGTH: 51
<212> TYPE: DNA
<213> ORGANISM: Artificial Sequence
<220> FEATURE:
<223> OTHER INFORMATION: hairpin loop oligonucleotide aptmer sequence
<220> FEATURE:
<221> NAME/KEY: modified_base
<222> LOCATION: (18)...(18)
<223> OTHER INFORMATION: I
<220> FEATURE:
<221> NAME/KEY: modified_base
<222> LOCATION: (35)...(35)
<223> OTHER INFORMATION: I
<220> FEATURE:
<221> NAME/KEY: misc_feature
<222> LOCATION: 18, 35
<223> OTHER INFORMATION: Inosine at positions 18 and 35

<400> SEQUENCE: 8
ggactactac tactactnat tcttagcgtt ttcantagta gtagtagtcc t          51

<210> SEQ ID NO 9
<211> LENGTH: 51
<212> TYPE: DNA
<213> ORGANISM: Artificial Sequence
<220> FEATURE:
<223> OTHER INFORMATION: hairpin loop oligonucleotide aptamer sequence
<220> FEATURE:
<221> NAME/KEY: modified_base
<222> LOCATION: (38)...(38)
<223> OTHER INFORMATION: I
<220> FEATURE:
<221> NAME/KEY: misc_feature
<222> LOCATION: (38)...(38)
<223> OTHER INFORMATION: Inosine at position 38

<400> SEQUENCE: 9
ggactactac tactactgat tcttagcgtt ttcagtanta gtagtagtcc t          51

<210> SEQ ID NO 10
<211> LENGTH: 51
<212> TYPE: DNA
<213> ORGANISM: Artificial Sequence
<220> FEATURE:
<223> OTHER INFORMATION: hairpin loop oligonucleotide aptamer sequence
<220> FEATURE:
<221> NAME/KEY: modified_base
<222> LOCATION: (41)...(41)
<223> OTHER INFORMATION: I
<220> FEATURE:
<221> NAME/KEY: misc_feature
<222> LOCATION: (41)...(41)
<223> OTHER INFORMATION: Inosine at position 41

<400> SEQUENCE: 10
ggactactac tactactgat tcttagcgtt ttcagtagta ntagtagtcc t          51

<210> SEQ ID NO 11
```

```
<211> LENGTH: 51
<212> TYPE: DNA
<213> ORGANISM: Artificial Sequence
<220> FEATURE:
<223> OTHER INFORMATION: hairpin loop oligonucleotide aptamer sequence

<400> SEQUENCE: 11
cctgatgatg atgatgacat tcttagcgtt ttgtcatcat catcatcagg t           51

<210> SEQ ID NO 12
<211> LENGTH: 51
<212> TYPE: DNA
<213> ORGANISM: Artificial Sequence
<220> FEATURE:
<223> OTHER INFORMATION: hairpin loop oligonucleotide aptamer sequence
<220> FEATURE:
<221> NAME/KEY: modified_base
<222> LOCATION: (13)...(13)
<223> OTHER INFORMATION: I
<220> FEATURE:
<221> NAME/KEY: misc_feature
<222> LOCATION: (13)...(13)
<223> OTHER INFORMATION: Inosine at position 13

<400> SEQUENCE: 12
cctgatgatg atnatgacat tcttagcgtt ttgtcatcat catcatcagg t           51

<210> SEQ ID NO 13
<211> LENGTH: 51
<212> TYPE: DNA
<213> ORGANISM: Artificial Sequence
<220> FEATURE:
<223> OTHER INFORMATION: hairpin loop oligonucleotide aptamer sequence
<220> FEATURE:
<221> NAME/KEY: modified_base
<222> LOCATION: (10)...(10)
<223> OTHER INFORMATION: I
<220> FEATURE:
<221> NAME/KEY: misc_feature
<222> LOCATION: (10)...(10)
<223> OTHER INFORMATION: Inosine at position 10

<400> SEQUENCE: 13
cctgatgatn atgatgacat tcttagcgtt ttgtcatcat catcatcagg t           51

<210> SEQ ID NO 14
<211> LENGTH: 51
<212> TYPE: DNA
<213> ORGANISM: Artificial Sequence
<220> FEATURE:
<223> OTHER INFORMATION: hairpin loop oligonucleotide aptamer sequence
<220> FEATURE:
<221> NAME/KEY: modified_base
<222> LOCATION: (7)...(7)
<223> OTHER INFORMATION: I
<220> FEATURE:
<221> NAME/KEY: misc_feature
<222> LOCATION: (7)...(7)
<223> OTHER INFORMATION: Inosine at position 7

<400> SEQUENCE: 14
cctgatnatg atgatgacat tcttagcgtt ttgtcatcat catcatcagg t           51

<210> SEQ ID NO 15
<211> LENGTH: 51
<212> TYPE: DNA
<213> ORGANISM: Artificial Sequence
<220> FEATURE:
<223> OTHER INFORMATION: hairpin loop oligonucleotide aptamer sequence
<220> FEATURE:
<221> NAME/KEY: modified_base
```

```
<222> LOCATION: (7)...(7)
<223> OTHER INFORMATION: I
<220> FEATURE:
<221> NAME/KEY: modified_base
<222> LOCATION: (10)...(10)
<223> OTHER INFORMATION: I
<220> FEATURE:
<221> NAME/KEY: misc_feature
<222> LOCATION: 7, 10
<223> OTHER INFORMATION: Inosine at positions 7 and 10

<400> SEQUENCE: 15
cctgatnatn atgatgacat tcttagcgtt ttgtcatcat catcatcagg t            51

<210> SEQ ID NO 16
<211> LENGTH: 51
<212> TYPE: DNA
<213> ORGANISM: Artificial Sequence
<220> FEATURE:
<223> OTHER INFORMATION: hairpin loop oligonucleotide aptamer sequence
<220> FEATURE:
<221> NAME/KEY: modified_base
<222> LOCATION: (7)...(7)
<223> OTHER INFORMATION: I
<220> FEATURE:
<221> NAME/KEY: modified_base
<222> LOCATION: (10)...(10)
<223> OTHER INFORMATION: I
<220> FEATURE:
<221> NAME/KEY: modified_base
<222> LOCATION: (13)...(13)
<223> OTHER INFORMATION: I
<220> FEATURE:
<221> NAME/KEY: modified_base
<222> LOCATION: (16)...(16)
<223> OTHER INFORMATION: I
<220> FEATURE:
<221> NAME/KEY: misc_feature
<222> LOCATION: 7, 10, 13, 16
<223> OTHER INFORMATION: Inosine at positions 7, 10, 13 and 16

<400> SEQUENCE: 16
cctgatnatn atnatnacat tcttagcgtt ttgtcatcat catcatcagg t            51

<210> SEQ ID NO 17
<211> LENGTH: 51
<212> TYPE: DNA
<213> ORGANISM: Artificial Sequence
<220> FEATURE:
<223> OTHER INFORMATION: hairpin loop oligonucleotide aptamer sequence
<220> FEATURE:
<221> NAME/KEY: modified_base
<222> LOCATION: (26)...(26)
<223> OTHER INFORMATION: I
<220> FEATURE:
<221> NAME/KEY: misc_feature
<222> LOCATION: (26)...(26)
<223> OTHER INFORMATION: Inosine at position 26

<400> SEQUENCE: 17
ggactactac tactactgat tcttancgtt ttcagtagta gtagtagtcc t            51

<210> SEQ ID NO 18
<211> LENGTH: 51
<212> TYPE: DNA
<213> ORGANISM: Artificial Sequence
<220> FEATURE:
<223> OTHER INFORMATION: hairpin loop oligonucleotide aptamer sequence
<220> FEATURE:
<221> NAME/KEY: modified_base
<222> LOCATION: (28)...(28)
<223> OTHER INFORMATION: I
<220> FEATURE:
```

```
<221> NAME/KEY: misc_feature
<222> LOCATION: (28)...(28)
<223> OTHER INFORMATION: Inosine at position 28

<400> SEQUENCE: 18
ggactactac tactactgat tcttagcntt ttcagtagta gtagtagtcc t       51

<210> SEQ ID NO 19
<211> LENGTH: 51
<212> TYPE: DNA
<213> ORGANISM: Artificial Sequence
<220> FEATURE:
<223> OTHER INFORMATION: hairpin loop oligonucleotide aptamer sequence
<220> FEATURE:
<221> NAME/KEY: modified_base
<222> LOCATION: (23)...(23)
<223> OTHER INFORMATION: I
<220> FEATURE:
<221> NAME/KEY: misc_feature
<222> LOCATION: (23)...(23)
<223> OTHER INFORMATION: Inosine at position 23

<400> SEQUENCE: 19
ggactactac tactactgat tcntagcgtt ttcagtagta gtagtagtcc t       51

<210> SEQ ID NO 20
<211> LENGTH: 51
<212> TYPE: DNA
<213> ORGANISM: Artificial Sequence
<220> FEATURE:
<223> OTHER INFORMATION: hairpin loop oligonucleotide aptamer sequence
<220> FEATURE:
<221> NAME/KEY: modified_base
<222> LOCATION: (24)...(24)
<223> OTHER INFORMATION: I
<220> FEATURE:
<221> NAME/KEY: misc_feature
<222> LOCATION: (24)...(24)
<223> OTHER INFORMATION: Inosine at position 24

<400> SEQUENCE: 20
ggactactac tactactgat tctnagcgtt ttcagtagta gtagtagtcc t       51

<210> SEQ ID NO 21
<211> LENGTH: 12
<212> TYPE: DNA
<213> ORGANISM: Artificial Sequence
<220> FEATURE:
<223> OTHER INFORMATION: hairpin loop oligonucleotide sequence

<400> SEQUENCE: 21
ttcttagcgt tt                                                   12

<210> SEQ ID NO 22
<211> LENGTH: 12
<212> TYPE: DNA
<213> ORGANISM: Artificial Sequence
<220> FEATURE:
<223> OTHER INFORMATION: hairpin loop oligonucleotide sequence
<220> FEATURE:
<221> NAME/KEY: modified_base
<222> LOCATION: (4)...(4)
<223> OTHER INFORMATION: I
<220> FEATURE:
<221> NAME/KEY: misc_feature
<222> LOCATION: (4)...(4)
<223> OTHER INFORMATION: Inosine at position 4

<400> SEQUENCE: 22
ttcntagcgt tt                                                   12
```

<210> SEQ ID NO 23
<211> LENGTH: 12
<212> TYPE: DNA
<213> ORGANISM: Artificial Sequence
<220> FEATURE:
<223> OTHER INFORMATION: hairpin loop oligonucleotide sequence
<220> FEATURE:
<221> NAME/KEY: modified_base
<222> LOCATION: (5)...(5)
<223> OTHER INFORMATION: I
<220> FEATURE:
<221> NAME/KEY: misc_feature
<222> LOCATION: (5)...(5)
<223> OTHER INFORMATION: Inosine at position 5

<400> SEQUENCE: 23
ttctnagcgt tt                                                           12

<210> SEQ ID NO 24
<211> LENGTH: 12
<212> TYPE: DNA
<213> ORGANISM: Artificial Sequence
<220> FEATURE:
<223> OTHER INFORMATION: hairpin loop oligonucleotide sequence
<220> FEATURE:
<221> NAME/KEY: modified_base
<222> LOCATION: (7)...(7)
<223> OTHER INFORMATION: I
<220> FEATURE:
<221> NAME/KEY: misc_feature
<222> LOCATION: (7)...(7)
<223> OTHER INFORMATION: Inosine at position 7

<400> SEQUENCE: 24
ttcttancgt tt                                                           12

<210> SEQ ID NO 25
<211> LENGTH: 12
<212> TYPE: DNA
<213> ORGANISM: Artificial Sequence
<220> FEATURE:
<223> OTHER INFORMATION: hairpin loop oligonucleotide sequence
<220> FEATURE:
<221> NAME/KEY: modified_base
<222> LOCATION: (4)...(4)
<223> OTHER INFORMATION: I
<220> FEATURE:
<221> NAME/KEY: modified_base
<222> LOCATION: (5)...(5)
<223> OTHER INFORMATION: I
<220> FEATURE:
<221> NAME/KEY: misc_feature
<222> LOCATION: 4, 5
<223> OTHER INFORMATION: Inosine at positions 4 and 5

<400> SEQUENCE: 25
ttcnnagcgt tt                                                           12

<210> SEQ ID NO 26
<211> LENGTH: 12
<212> TYPE: DNA
<213> ORGANISM: Artificial Sequence
<220> FEATURE:
<223> OTHER INFORMATION: hairpin loop oligonucleotide sequence
<220> FEATURE:
<221> NAME/KEY: modified_base
<222> LOCATION: (4)...(4)
<223> OTHER INFORMATION: I
<220> FEATURE:
<221> NAME/KEY: modified_base
<222> LOCATION: (7)...(7)

```
<223> OTHER INFORMATION: I
<220> FEATURE:
<221> NAME/KEY: misc_feature
<222> LOCATION: 4, 7
<223> OTHER INFORMATION: Inosine at positions 4 and 7

<400> SEQUENCE: 26
ttcntancgt tt                                                              12

<210> SEQ ID NO 27
<211> LENGTH: 12
<212> TYPE: DNA
<213> ORGANISM: Artificial Sequence
<220> FEATURE:
<223> OTHER INFORMATION: hairpin loop oligonucleotide sequence
<220> FEATURE:
<221> NAME/KEY: modified_base
<222> LOCATION: (5)...(5)
<223> OTHER INFORMATION: I
<220> FEATURE:
<221> NAME/KEY: modified_base
<222> LOCATION: (7)...(7)
<223> OTHER INFORMATION: I
<220> FEATURE:
<221> NAME/KEY: misc_feature
<222> LOCATION: 5, 7
<223> OTHER INFORMATION: Inosine at positions 5 and 7

<400> SEQUENCE: 27
ttctnancgt tt                                                              12

<210> SEQ ID NO 28
<211> LENGTH: 12
<212> TYPE: DNA
<213> ORGANISM: Artificial Sequence
<220> FEATURE:
<223> OTHER INFORMATION: hairpin loop oligonucleotide sequence
<220> FEATURE:
<221> NAME/KEY: modified_base
<222> LOCATION: (4)...(4)
<223> OTHER INFORMATION: I
<220> FEATURE:
<221> NAME/KEY: modified_base
<222> LOCATION: (5)...(5)
<223> OTHER INFORMATION: I
<220> FEATURE:
<221> NAME/KEY: modified_base
<222> LOCATION: (7)...(7)
<223> OTHER INFORMATION: I
<220> FEATURE:
<221> NAME/KEY: misc_feature
<222> LOCATION: 4, 5, 7
<223> OTHER INFORMATION: Inosine at positions 4, 5 and 7

<400> SEQUENCE: 28
ttcnnancgt tt                                                              12

<210> SEQ ID NO 29
<211> LENGTH: 39
<212> TYPE: DNA
<213> ORGANISM: Artificial Sequence
<220> FEATURE:
<223> OTHER INFORMATION: oligonucleotide probe sequence
<220> FEATURE:
<221> NAME/KEY: misc_feature
<222> LOCATION: (37)...(37)
<223> OTHER INFORMATION: FAM-labelled at position 37

<400> SEQUENCE: 29
tttttttttt ttttttttt gcagggccga aggcccugc                                   39
```

```
<210> SEQ ID NO 30
<211> LENGTH: 59
<212> TYPE: DNA
<213> ORGANISM: Artificial Sequence
<220> FEATURE:
<223> OTHER INFORMATION: oligonucleotide probe
<220> FEATURE:
<221> NAME/KEY: misc_feature
<222> LOCATION: (37)...(37)
<223> OTHER INFORMATION: FAM-labelled at position 27

<400> SEQUENCE: 30
tttttttttt tttttttttt gcagggccga aggcccugca aaaaaaaaaa aaaaaaaaa         59
```